(12) United States Patent
Kartalov et al.

(10) Patent No.: US 8,361,738 B2
(45) Date of Patent: Jan. 29, 2013

(54) METHODS FOR QUANTITATIVE TARGET DETECTION AND RELATED DEVICES AND SYSTEMS

(75) Inventors: Emil P. Kartalov, Pasadena, CA (US); Axel Scherer, Laguna Beach, CA (US); Clive Taylor, Malibu, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 282 days.

(21) Appl. No.: 12/717,402

(22) Filed: Mar. 4, 2010

(65) Prior Publication Data

US 2010/0267064 A1  Oct. 21, 2010

Related U.S. Application Data

(60) Provisional application No. 61/209,531, filed on Mar. 6, 2009.

(51) Int. Cl.
*G01N 33/00* (2006.01)

(52) U.S. Cl. .................................... 435/7.94

(58) Field of Classification Search ................ None
See application file for complete search history.

(56) References Cited

U.S. PATENT DOCUMENTS

| | | | | |
|---|---|---|---|---|
| 2001/0026929 A1* | 10/2001 | Yang et al. | ...................... | 435/23 |
| 2003/0199100 A1* | 10/2003 | Wick | ............................ | 436/153 |
| 2004/0067502 A1* | 4/2004 | Guenther et al. | ................. | 435/6 |
| 2006/0127238 A1* | 6/2006 | Mosier et al. | ................. | 417/313 |
| 2008/0013092 A1 | 1/2008 | Maltezos et al. | ............. | 356/417 |

OTHER PUBLICATIONS

Kartalov et al., High-throughput multi-antigen microfluidic fluorescence immunoassays, 2006, Biotechniques, 40(1): pp. 85-90.*
Kartolov et al., Internally calibrated quantification of protein analytes in human serum by fluorescence immunoassays in disposable elastomeric microfluidic devices, 2008, Electrophoresis, 29: pp. 5010-5016.*
H.C. Gilbert, J.W. Szokol, Int. Anesthesiol. Clin. 42 (2) (2004) 73.
Kartalov, E.P., Multiplexed microfluidic immunoassays for point-of-care in vitro diagnostics, *In-Vitro Diagn. Technol.* vol. 103, No. 33, Aug. 15, 2006, 12280-12284.
Wang, J., et al., Electrochemical Enzyme Immunoassays on Microchip Platforms, *Anal. Chem.* 73 (2001) 5323-5327.
Fruetel, J.A., et al., Microchip separations of protein biotoxins using an integrated hand-held device, *Electrophoresis* 26 (2005) 1144-1154.
Angenendt, P., et al., 3D Protein Microarrays: Performing Multiplex Immunoassays on a Single Chip, *Anal. Chem.* 75 (2003) 4368-4372.
Delehanty, J.B., et al., A Microarray Immunoassay for Simultaneous Detection of Proteins and Bacteria, *Anal. Chem.* 74 (2002) 5681-5687.
Sapsford, K.E., et al., Demonstration of Four Immunoassay Formats Using the Array Biosensor, *Anal. Chem.* 74 (2002) 1061-1068.
Sydor, J.R., et al., Chip-Based Analysis of Protein-Protein Interactions by Fluorescence Detection and On-Chip Immunoprecipitation Combined with μLC-MS/MS Analysis, *Anal. Chem.* 75 (2003) 6163-6170.
Holmes, D., et al., Bead-based immunoassays using a micro-chip flow cytometer†, *Lab Chip* 7 (2007) 1048-1056.
Herr, A.E., et al., On-Chip Native Gel Electrophoresis-Based Immunoassays for Tetanus Antibody and Toxin, *Anal. Chem.* 77 (2005) 585-590.

(Continued)

*Primary Examiner* — Nelson C. Yang
(74) *Attorney, Agent, or Firm* — Steinfl & Bruno LLP

(57) ABSTRACT

Described herein is a method for detection of a target in a sample and related devices and systems.

10 Claims, 9 Drawing Sheets

OTHER PUBLICATIONS

Wolf, M., et al., Simultaneous detection of C-reactive protein and other cardiac markers in human plasma using micromosaic immunoassays and self-regulating microfluidic networks, Biosensors and Bioelectronics 19 (2004) 1193-1202.

Yakovleva, J., et al., Microfluidic Enzyme Immunoassay Using Silicon Microchip with Immobilized Antibodies and Chemiluminescence Detection, Anal. Chem. 74 (2004) pp. 2994-3004.

Chandrasekaran, A., et al., Hybrid Integrated Silicon Microfluidic Platform for Fluorescence Based Biodetection, Sensors 7 (2007) pp. 1901-1915.

Wang, Z.H., et al., A label-free protein microfluidic array for parallel immunoassays, Electrophoresis 27 (2006) pp. 4078-4085.

Misiakos, K., et al., A Monolithic Silicon Optoelectronic Transducer as a Real-Time Affinity Biosensor, Anal. Chem. 76 (2004) pp. 1366-1373.

Delamarche, E., et al., Patterned Delivery of Immunoglobulins to Surfaces Using Microfluidic Networks, Science 276 (1997) 779.

Eteshola, E., et al., Microfluidic ELISA: On-Chip Fluorescence Imaging, *Biomedical Microdevices* 6 (1) (2004) pp. 7-9.

Phillips, K.S., et al., Microfluidic Immunoassay for Bacterial Toxins with Supported Phospholipid Bilayer Membranes on Poly(dimethylsiloxane), *Anal. Chem.* 77 (2005) pp. 327-334.

Piyasena, M.E., et al., Near-Simultaneous and Real-Time Detection of Multiple Analytes in Affinity Microcolumns, *Anal. Chem.* 76 (2004) pp. 6266-6273.

Kanda, V., et al., Label-Free Reading of Microarray-Based Immunoassays with Surface Plasmon Resonance Imaging, *Anal. Chem.* 76 (2004) pp. 7257-7262.

Sia, S.K., et al., An Integrated Approach to a Portable and Low-cost Immunoassay for Resource-Poor Settings, *Angew. Chem. Int. Ed.* 43 (2004) pp. 498-502.

X. Jiang, et al., A Miniaturized, Parallel, Serially, Diluted Immunoassay for Analyzing Multiple Antigens, *J. Am. Chem. Soc.* 125 (2003) pp. 5294-5295.

Herrmann, M., et al., Enzymatically-generated fluorescent detection in micro-channels with internal magnetic mixing for the development of parallel microfluidic ELISA, *Lab Chip* 6 (2006) pp. 555-560.

Herrmann, M., et al., Microfluidic ELISA on non-passivated PDMS chip using magnetic bead transfer inside dual networks of channels, *Lab Chip* 7 (2007) pp. 1546-1552.

Kurita, R., et al., On-Chip Enzyme Immunoassay of a Cardiac Marker Using a Microfluidic Device Combined with a Portable Surface Plasmon Resonance System, *Anal. Chem.* 78 (2006) pp. 5525-5531.

Y.J. Liu, et al., Integration of minisolenoids in microfluidic device for magnetic bead-based immunoassays, *J. Appl. Phys.* 102 (2007) 084911.

Sui, G., et al., Solution-Phase Surface Modification in Intact Poly(dimethylsiloxane) icrofluidic Channels, Anal. Chem. 78 (2006) pp. 5543-5551.

Linder, V., et al., Application of surface biopassivated disposable poly(dimethylsiloxane)/glass chips to a heterogeneous competitive human serum immunoglobulin G immunoassay with incorporated internal standard, Electrophoresis 23 (2002) pp. 740-749.

F.Y.H. Lin, et al., Development of a novel microfluidic immunoassay for the detection of *Helicobacter pylori* infection, *Analyst* 129 (2004) pp. 823-828.

Nashida, N., et al., Electrochemical immunoassay on a microfluidic device with sequential injection and flushing functions, Biosensors and Bioelectronics 22 (2007) pp. 3167-3173.

Lucas, L.J., et al., Lab-on-a-chip immunoassay for multiple antibodies using microsphere light scattering and quantum dot emission, Biosensors and Bioelectronics 23 (2007) pp. 675-681.

Murphy, B.M., et al., Competitive Immunoassays for Simultaneous Detection of Metabolites and Proteins Using Micromosaic Patterning, Anal. Chem. 80 (2008) pp. 444-450.

S.H. Kim, et al., Simple Route to Hydrophilic Microfluidic Chip Fabrication using an Ultraviolet (UV)- Cured Polymer, *Adv. Funct. Mater.* 17 (2007) pp. 3493-3498.

Y. Bai, et al., Surface Modification for Enhancing Antibody Binding on Polymer-Based Microfluidic Device for Enzyme-Linked Immunosorbent Assay, *Langmuir* 22 (2006) pp. 9458-9467.

Nelson, K.E., et al., Concentration Gradient Immunoassay. 1. An Immunoassay Based on Interdiffusion and Surface Binding in a Microchannel, Anal. Chem. 79 (2007) pp. 3542-3548.

M.J. Pugia, et al., Microfluidic Tool Box as Technology Platform for Hand-Held Diagnostics, *Clin. Chem.* 51 (10) (2005) 1923.

Bhattacharyya, A. et al., Design and testing of a disposable microfluidic chemiluminescent immunoassay for disease biomarkers in human serum samples, Biomed Microdevices 9 (2) (2007) pp. 245-251.

Liang, K., et al., Simultaneous detection of five indices of hepatitis B based on an integrated automatic microfluidic device, Biomed Microdevices 9 (3) (2007) pp. 325-333.

N. Honda, U. Linberg, P. Andersson, S. Hoffmann, H. Takei, Simultaneous Multiple Immunoassays in a Compact Disc-Shaped Microfluidic Device Based on Centrifugal Force, *Clin. Chem.* 51 (10) (2005) pp. 1955-1961.

Mulvaney, S.P., et al., Rapid, femtomolar bioassays in complex matrices combining microfluidics and magnetoelectronics, *Biosensors and Bioelectronics* 23 (2007) pp. 191-200.

H. Dong, et al., Screen-printed microfluidic device for electrochemical immunoassay, *Lab on a Chip* 7 (2007) pp. 1752-1758.

R. Fan, O. Vermesh, A. Srivastava, B.K.H. Yen, L. Qin, H. Ahmad, G.A. Kwong, C.C.Liu, J. Gould, L. Hood, J.R. Heath, Integrated barcode chips for rapid, multiplexed analysis of proteins in microliter quantities of blood, *Nat. Biotechnol.* 26 (12) (2008) pp. 1373-1378.

E.P. Kartalov, J.F. Zhong, A. Scherer, S.R. Quake, et al., High-throughput multi-antigen microfluidic fluorescence immunoassays, *Biotechniques* 40 (1) (2006) pp. 85-90.

Kartalov, E.P., et al. Internally calibrated quantification of protein analytes in human serum by fluorescence immunoassays in disposable elastomeric microfluidic devices, *Electrophoresis* 29 (2008) pp. 5010-5016.

H.G. Hotz, O.J. Hines, R. Masood, B. Hotz, T. Foitzik, H.J. Buhr, P.S. Gill, H.R. Reber, Surgery 137 (2) (2005) 192.

A.M. Levine, et al., Phase I Study of Antisense Oligonucleotide Against Vascular Endothelial Growth Factor: Decrease in Plasma Vascular Endothelial Growth Factor with Potential Clinical Efficacy, *J. Clin. Oncol.* 24 (2006) pp. 1712-1719.

V. VanDelinder, A. Groisman, Separation of Plasma from Whole Human Blood in a Continuous Cross-Flow in a Molded Microfluidic Device Anal. Chem. 78 (2006) pp. 3765-3771.

E.P. Kartalov, W.F. Anderson, A. Scherer, J. The Analytical Approach to Polydimethylsiloxane Microfluidic Technology and its Biological Applications, *Nanosci. Nanotechnol.* 6 (8) (2006) 2265.

Belfort, et al., The behavior of suspensions and macromolecular solutions in crossflow microfiltration, *J. Membr. Sci.* 96, 1-58 (1994).

Zydney, A.L., et al., Continuous flow membrane plasmapheresis: theoretical models for flux and hemolysis prediction, *Trans. Am. Soc. Artif. Intern. Organs* 28, 408-412 (1982).

Lin, D.H., et al., Internally calibrated quantification of VEGF in human plasma by fluorescence immunoassays in disposable elastomeric microfluidic devices, *J Chromatography B.*, 2009.

Hansen, C.L., et al., Systematic investigation of protein behavior with a microfluidic formulator, 2004, vol. 101:40, pp. 14431-14436.

Armani A.M., et al., Label-free, single-molecule detection with optical microcavities, Science, vol. 317 Aug. 10, 2007, pp. 783.

Unger, M.A., et al., Monolithic Microfabricated Valves and Pumps by Multilayer Soft Lithography, Science 2000, vol. 288, pp. 113-116.

Kartalov, E.P., Microfluidic vias enable nested bioarrays and autoregulatory devices in Newtonian fluids, Proc. Nat/Acad. Sci. USA 2006, 103, pp. 12280-12284.

Henderson, L.W. et al. *Hemofiltration*, Springer-Verlag, Germany 1986.

* cited by examiner

METHODS FOR QUANTITATIVE TARGET DETECTION AND RELATED DEVICES AND SYSTEMS

CROSS REFERENCE TO RELATED APPLICATIONS

This application claims priority to U.S. provisional application Ser. No. 61/209,531, filed on Mar. 6, 2009 entitled "Internally Calibrated quantification of protein analytes in human plasma by fluorescence immunoassay in elastomeric microfluidic devices", docket number CIT5090-P2 incorporated herein by reference in its entirety.

STATEMENT OF GOVERNMENT GRANT

The U.S. Government has certain rights in this invention pursuant to Grant No(s). EB007151 and HG002644 awarded by National Institutes of Health.

FIELD

The present disclosure relates to quantitative target detection and in particular to methods for quantitative detection and related devices and systems.

BACKGROUND

High sensitivity detection of targets and in particular of biomarkers has been a challenge in the field of biological molecule analysis, in particular when aimed at detection of a plurality of targets. Whether for pathological examination or for fundamental biology studies, several methods are commonly used for the detection of various classes of biomaterials and biomolecules.

In several applications, including in particular those for which ubiquitous testing is desirable, the current biological techniques has been reduced from the macro- to the microscale, and more particularly in multi-analyte high-throughput handheld devices. In particular, reducing assays (e.g. immunoassays) to microfluidic scale has been extensively explored in recent years. In spite of various efforts and products, the capability to measure multiple antigens and samples per device, an industrially feasible fabrication, parsimony of sample and reagents, adequate sensitivity and specificity, and/or adequate reliability and reproducibility still remain a challenge.

SUMMARY

Provided herein, are microfluidic devices, methods and systems that in several embodiments, allow reproducible quantification of targets even in complex fluids such as human serum or other bodily fluids in elastomeric microfluidic devices.

According to a first aspect, a method to detect a target in a sample is described. The method comprises dividing the sample in a plurality of subsamples, and adding to the subsamples a set quantity of the target and/or analog thereof, the subsamples comprising a subsample with no target nor analog thereof added thereto. The method further comprises detecting the target and/or analog thereof in each subsample thus providing a set of detection signal comprising a detection signal related to the subsample with no target nor analog thereof added thereto; and subtracting a background signal from each detection signal to provide a set of net signals. The method also comprises: providing a distribution of signal points, each signal point based on a net signal of the set of net signals, the signal points comprising a signal point related to the subsample with no target nor analog thereof added thereto the distribution having a slope. The method additionally comprises determining the endogenous target concentration in the sample by dividing the amplitude of the signal point related to the subsample with no target nor analog thereof added thereto by the slope of the distribution.

According to a second aspect, a system to detect a target in a sample is described. The system comprises at least two pre quantified targets and/or target analogs, and suitable reagents for target detection, the targets and suitable reagents being for simultaneous combined or sequential use in a method herein described.

The devices methods and systems herein described allow in several embodiments, reliable and cost effective testing systems that also allow reproducible quantification of complex sample such as human bodily fluid or a derivative thereof (e.g. plasma), and in particular human serum.

Furthermore, the devices methods and systems herein described allow in several embodiments, measurement of multiple antigens and samples per device, with sensitivity specificity, reliability and reproducibility.

The devices methods and systems herein described can be used in connection with applications wherein operation of a microfluidic device is desired, including for example performance of various kind of assays in a microfluidic environment, including high throughput, multiplexed assays, directed for example to target detection. As a consequence, exemplary fields where the power source, arrangements, methods and devices herein described can be used include medical, diagnostics, biological research, and veterinary.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

Figure 1A:
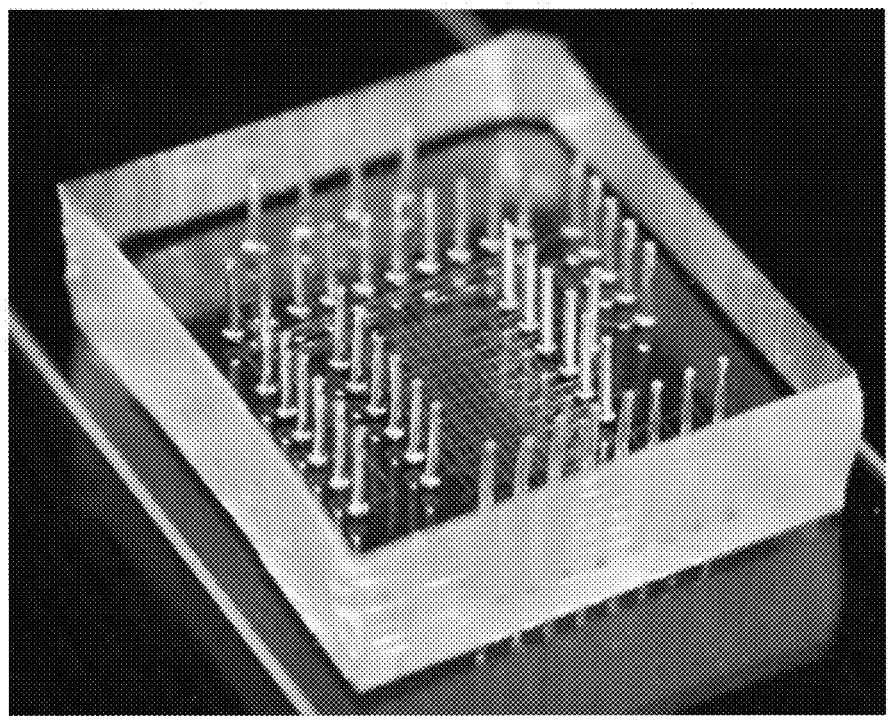
FIG. 1A shows a top perspective view of a microfluidic chip according to some embodiments herein described. A 60-chamber PDMS chip bound to a one-inch-wide epoxide slide was used for the experiments. The vertical cylinders are input ports for reagents and control pressure. The microchannel test matrix is visible in the middle.

Provided herein are devices methods and systems for internally calibrated quantitative detection of targets in microfluidic devices.

The term "detect" or "detection" as used herein indicates the determination of the existence, presence or fact of a target or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "target" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, aminoacids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof. Exemplary samples comprise whole blood, serum, plasma, cerebrospinal fluid, saliva, urine, vaginal fluid, sweat, oral swab extract, tears, and biopsy samples.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer or oligopeptide. As used herein the term "amino acid", "amino acidic monomer", or "amino acid residue" refers to any of the twenty naturally occurring amino acids including synthetic amino acids with unnatural side chains and including both D an L optical isomers. The term "amino acid analog" refers to an amino acid in which one or more individual atoms have been replaced, either with a different atom, isotope, or with a different functional group but is otherwise identical to its natural amino acid analog.

In particular according to some embodiments a recalibration method for quantitative detection of targets is described. In some embodiments, the recalibration method involves dividing the sample in subsample and adding a set quantity such as a known concentration of the target or of an appropriate analog of the analyte of interest in the subsamples.

The term "analog" as used herein indicates structural analogs (structural analogues), also known as chemical analogs or simply analogs, i.e. compounds in which one or more atoms, functional groups, or substructures of the reference compound have been replaced with different atoms, groups, or substructures and that retains the ability of the reference compound of being detected by suitable detection techniques. Despite a high chemical similarity, structural analogs are not necessarily functional analogs, and vice versa, and can have same or different physical, chemical, biochemical, or pharmacological properties. For example, in some embodiments, the term analog refers to commercially available protein that mimics a naturally endogenously occurring antigen in that it has the same relevant biochemical reactivities, e.g. to antibodies against the natural antigen.

In some embodiments, the appropriate concentration of the analyte of interest or analog thereof used for spiking the sample is selected in view of the concentration of the target to be detected. In particular, the set quantity of target or analog added to the subsamples are selected to encompass a range including the biomedically normal concentration (or concentration range) of the target to be detected (see e.g. Examples 4 and 8). In some embodiments, a range of spiking concentrations is selected to encompass at least one order of magnitude above and one order of magnitude below the biomedically normal concentration or range. In some embodiments, at least one of the subsamples (herein also referred as zero-spike) has no target added thereto.

In some embodiments, a background signal (signal from the environment where the detection is performed in absence of the sample) is detected using a labeling technique. The terms "label" and "labeled molecule" as used herein as a component of a complex or molecule refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence. As a consequence the wording and "labeling signal" as used herein indicates the signal emitted from the label that allows detection of the label, including but not limited to radioactivity, fluorescence, chemoluminescence, production of a compound in outcome of an enzymatic reaction and the likes. Exemplary labeling techniques comprise fluorescence immunoassays (e.g. sandwich immunoassays as the approach of chemical recognition In particular in some exemplary embodiments, dyes are typically detected optically; nanoparticles can be detected optically, electronically, or magnetically; enzyme products can be detected optically (e.g. chemiluminescence) or electronically (e.g. redox combined with conductance measurement); radioactive labels are typically detected by photographic plates and additional techniques that allow quantitation through calibration.

In some embodiments, the background signal can be detected by detecting the non specific binding of the labeled molecule e.g. by detecting the signal of a buffer solution in the vessel or chamber where the target detection is performed or by other approaches identifiable by a skilled person.

In some embodiments, following addition of the target/analog to the subsamples (spiking) the target in the sample is quantified by the same labeling technique used for detecting the background signal from a control measurement to originate a signal point or datapoint, corresponding to the spiked sample. In some embodiments, the background signal is then subtracted from the signal point to provide a net signal.

In some embodiments, a detection signal from the zero-spike sample and a detection signal from a spiked sample are derived. The background signal is then subtracted from both zero-spike and spiked signals to get net zero-spike signal and net spiked signal. The endogenous concentration is then calculated and in some embodiments, is equal to the spiking concentration multiplied by the net zero-spike signal and divided by the difference between net spiked and net zero-spike signals.

In some embodiments, the resulting net signals are plotted against the respective spiking concentrations on a same distribution which comprises at least in a portion a linear fit.

The specific type of distribution is typically functional to the specific concentration selected to spike the subsamples. In some embodiments, the distribution is provided by a linear graph (see e.g. Examples 4 and 8).

In particular, in some embodiments, the datapoint derived from the signal detection produce, in at least portion of the distribution, a linear fit having a slope, which on its turn produces a value for the slope.

In some embodiments, the zero-spike signal is divided by the slope to produce the endogenous concentration of the target detected with the method herein described.

In some embodiments, multi-analyte measurements are performed. In some of those embodiments, the same sample containing multiple analytes is aliquoted in subsamples, and each aliquot is spiked with several analogs (one for each analyte of interest), and then each subsample is measured against each analyte. In some of those embodiments, a separate recalibration curve is plotted for each analyte.

In several embodiments, the methods herein described wherein the sample is aliquoted in subsamples and spiked with a plurality of concentrations of the target/analog, to produce a calibration curve instead of a single-point standard, accounting for potential non-linear response of the system, e.g. saturation at very high values. In such saturation cases, the linear section of the calibration curve is used to extract the slope for purposes of calculating the endogenous concentration, while the saturating e.g. asymptotic section is not used. Some of those embodiments also allow that the subsamples have the same biochemical ambience, reducing the influence of biological variability among standards and unknown samples.

Additionally, the method wherein detection is performed on subsamples in several embodiments can minimize the negative effects of variations in the antibody activity among subsamples, in particular when detection is performed in parallel. For example, if according to a certain experimental settings antibodies are used as capture agents for detection and the antibody activity has declined by a certain factor during the experiment, the signals from the subsamples are expected to decrease by the same factor, and so is the slope to the fit. In particular, since in several embodiments, the endogenous amount or concentration of the target is calculated as the ratio of zero-spike signal to slope value, both of which are decreased by the same factor, the impact of that factor is minimized and even cancelled leaving the quantitative detection minimally or not at all affected by the variations in antibody activity between experiments. Accordingly, in several embodiments where detection is performed on subsamples the impact of antibody activity and similar sources of variation on the final detection is minimized.

In some embodiments, the recalibration scheme involving spiking of subsamples is compatible with parallelization in multi-analyte format. For example, the same subsamples can be simultaneously spiked with several analogs, each to a different analyte of interest. Then simultaneous recalibrations can be performed on the same chip, simply by measuring each of the subsamples against multiple analytes of interest. Then for each analyte of interest, there would be a separate recalibration curve. Thus in several embodiments, the recalibration scheme has an inherent property of orthogonality, so long as there is no cross-reactivity between an antibody of one analyte with another analyte. In some embodiments, the orthogonality of immunoassays thus carries over to orthogonality of the recalibration scheme and allows multi-analyte high-throughput applications.

In some embodiments, spiking of a sample and detection of the target/analog is preceded by sample collection and sample preparation.

In particular sample collection can be performed using techniques known to the skilled person. In some embodiments, sample-preparation can be performed by collecting unprocessed sample into a measurement-usable sample by a separation process, e.g. by head-on filtration or cross-flow filtration. In some of those embodiments the sample is whole blood that is converted to plasma by adding an anticoagulant (e.g. heparin, citric acid) before, during, or after the separation process.

In some embodiments, the anticoagulant can be introduced into the sample by depositing it in lyophilized form on the fluidic pathway of the sample. In some embodiments the anticoagulant is introduced during sample collection, e.g. lyophilized inside the needle or tube that takes up the whole blood from the patient.

In some embodiments, the spiking stage involves the splitting of the sample into subsamples, and the introduction of known amounts of biochemical analog to the analyte of interest into these subsamples.

In several embodiments, detection is performed by providing labeled capture agents or other labeled molecules that are capable to specifically bind and are therefore specific for the target to be detected. The wording "specific" "specifically" or specificity" as used herein with reference to the binding of a molecule to another refers to the recognition, contact and formation of a stable complex between the molecule and the another, together with substantially less to no recognition, contact and formation of a stable complex between each of the molecule and the another with other molecules. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence.

In some embodiments, the detection is performed by immunoassays with detection output based on fluorescence, chemi-luminescence, photonics, and/or electrical measurements such as redox, conductance, resistance, and capacitance.

In some embodiments, where the subsamples are measured separately (e.g. by one or more of the methods herein described), the signals are reduced by ambient background signals, the resulting net signals are plotted against spiking amounts or concentrations, a linear fit is constructed to those datapoints, and the zero-spike net signal is divided by the slope of the linear fit to obtain the endogenous amount or concentration of the analyte of interest (internal recalibration scheme).

In some embodiments, the output stage produces a processed sample, a measurement, or both.

In some embodiments, the measurements are performed for each analyte with a panel of different antibodies against the same analyte.

The method to quantitatively detect target herein described can be performed with various devices comprising, for example, microtiter plates, microfluidic devices of various kind, and additional devices identifiable by a skilled person upon reading of the present disclosure.

In particular, in some embodiments, the methods herein described can be performed on microfluidic chips. The term "microfluidic" as used herein refers to a component or system that has microfluidic features e.g. channels and/or chambers that are generally fabricated on the micron or sub-micron scale. For example, the typical channels or chambers have at least one cross-sectional dimension in the range of about 0.1 microns to about 1500 microns, more typically in the range of about 0.2 microns to about 1000 microns, still more typically in the range of about 0.4 microns to about 500 microns. Individual microfluidic features typically hold very small quantities of fluid, e.g. from about 10 nanoliters to about 5 milliliters, more typically from about 100 nanoliters to about 2 milliliters, still more typically from about 200 nanoliters to about 500 microliters, or yet more typically from about 500 nanoliters to about 200 microliters.

In particular in some embodiments, methods herein described can be performed on the microfluidic chip described in [ref. 42] herein incorporated by reference in its entirety. In some embodiments, a particular device can be engineered to the specifications set by the recalibration method on the one hand, and the intended ability to measure multiple analytes, on the other hand. For example in some embodiments, a microfluidic device such as the one described in [ref. 42] is modified to include fewer coliseums, and modified chambers as illustrated for example in the Examples section (see e.g. Examples 1 and 5).

In some embodiments, the method herein described can be performed with a particular microfluidic device formed by a three-layer system, containing two PDMS (polydimethylsiloxane) layers and one glass substrate. In some of those embodiments, the glass substrate can be coated with protein-binding surface chemistry. The PDMS layer contacting the glass contains reagent channels, which are used to convey reagents to and from the glass surface. The second PDMS layer can be situated on top of the first PDMS layer and contain control channels that convey water as hydraulic working fluid to drive microfluidic valves. Each valve is a thin membrane vertically separating the channel that controls the valve from the reagent channel that the valve controls. In some embodiments, the chip works essentially as a two-dimensional matrix in which reagent channels carrying antibodies cross reagent channels carrying analytes, so that a reaction chamber is formed at each intersection. In some of those embodiments, access to each chamber is controlled by two sets of two valves, which function like traffic lights. After feeds are done in the correct sequence, labels detection from each reaction chambers forms the experimental data used to extract the endogenous concentrations of each analyte.

In some embodiments, the analog amounts are introduced by positioning them in lyophilized form on the fluidic pathway of the subsamples from input towards the measurement stage.

In some embodiments, the analog amounts are introduced in the subsamples by microfluidic metering techniques.

In some embodiments, multiple analytes are processed and/or measured within the same chip, in parallel or in series.

In some embodiments, antibodies against different analytes are simultaneously fed in parallel into channels whose surface is coated with a surface chemistry that immobilizes the antibodies. In some embodiments, a washing step removes unreacted excess material and passivates the surface against further bonding. In some embodiments, samples containing endogenous analytes of interest are spiked with varying known concentrations of analogs and are fed into the chip perpendicularly to the antibody channels, thereby producing a two-dimensional microfluidic test matrix. In some embodiments, analytes and analogs are allowed to bind to the respective antibodies and the excess material is washed away. In some embodiments, labeled capture agents such as antibodies to the same analytes are fed along the antibody channels and allowed to bind to the bound analytes and bound analogs to complete the sandwich immunoassays. In some embodiments, excess is washed away and detection by the label produces signal for each spiking concentration for each analyte. In some embodiments, a recalibration curve for each analyte shows signal versus spiking concentration and a linear fit to the curve produces a slope, the zero-spike signal is divided by the slope value to calculate the endogenous concentration. The same method can be applied to all analytes. In the particular device, arrays of microfluidic valves can be integrated to control fluid flow during the above procedure. Also, in the particular device, fluorescence can be used for labeling and quantification. However, other techniques of labeling would work as well, e.g. redox electrical detection, chemi-luminescence, nephelometry, conductance or capacitance measurements, or radioactivity.

In the particular embodiment, the aliquoting can be performed off-chip, or on-chip as well. In the particular embodiment, only one analyte per chip can be detected, so that multiple identical experiments can performed within the same chip. In particular, in some embodiments, the device can handle five or more different analytes at the same time. In the particular embodiment, one unspiked (zero-spike) sample can be analyzes with five spiked subsamples. In another embodiment a chip can be expanded with more coliseums to accommodate even more spiking for an even higher quality recalibration curve (more datapoints).

Some embodiments where the methods and systems are performed in microfluidic format can allow a significant reduction in the material requirements for reagent amounts and sample volumes. The parsimony in reagents allows for reduction in cost per test, while the parsimony of sample volume allows for measurements of samples that cannot be measured by conventional means (e.g. at the macro-scale). Further, the shrinkage of scale and the miniaturized fluidic control (e.g. through pneumatic monolithic microvalves) allow for parallelization of measurements, e.g. in a multi-analyte format, so that the same small amount of sample can be used by the particular device to quantify multiple analytes of interest. This parallelization ensures further reduction in costs as well as makes it possible to provide more diagnostic information with faster turnaround at lower costs. Finally, the shrinkage of scale and the inexpensiveness of the devices mean that the overall diagnostic systems can be made portable, widely available, and simple to use, e.g. in near-patient or point-of-care settings.

According to some embodiments a system for quantitative detection is described. The system comprises at least two of pre quantified targets and/or target analog, and suitable reagents for target detection, the prequantified targets and suitable reagents for simultaneous combined or sequential use in the methods for quantitatively detect a target herein described.

In some embodiments, a labeling molecule can also be included in the system herein disclosed, which include but not limited to labeled polynucleotides, labeled antibodies, other labels identifiable by the skilled person upon reading of the present disclosure.

Additional components can include a microfluidic chip (and in particular a device herein described), suitable reagents, targets, target analogs, alone or together with vehicles in compositions, fluorescent dyes or other labels, reference standards (and in particular reference standard for providing a distribution based on the detected signal) and additional components identifiable by a skilled person upon reading of the present disclosure.

In some embodiments the systems herein described can be provided in the form of a kit of parts, wherein the reagents are comprised in the kit independently.

In particular, the components of the kit can be provided, with suitable instructions and any other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable vehicles or auxiliary agent of the compositions comprising the target, or target analogs, capture agents such as antibodies or other reagents for the quantitative detection, and generally manufacturing and packaging of the kit, can be identified by the person skilled in the art upon reading of the present disclosure.

In several embodiments, the devices methods and system can be used to perform reliable quantitative detection with biomedical samples. In particular, in some embodiments, methods and systems herein described can be applied for reliable target detection in whole blood, serum, plasma, urine, saliva, cerebrospinal fluid, vaginal fluid, sweat, tears, swab extract, and similarly complexed samples.

In some embodiments, sample preparation can be performed by conventional macro-scale methods. For example, serum preparation from whole blood involves centrifugation of the coagulated material, and only after that can the serum be inserted in the measurement device. In some embodiments sample-preparation can be performed through microfluidic methods and systems that can complement the capabilities of microfluidic measurement devices.

In some embodiments, sample preparation device can be integrated in the same device, to simplify handling and to minimize sample wastage.

In some embodiments, where each sample-test combination is performed in a separate vessel (e.g. a separate microfluidic chamber), identification of the sample can be performed based on location, while the magnitude of the signal correlates with the amount of captured analyte. In some of those embodiments, the devices, methods and system can be associated, with a corresponding decrease in cost and ease of miniaturization with respect to methods that require multi-color fluorescence detection. In some embodiments, the devices methods and system achieves recalibration and higher sensitivity, while still working with a single type of fluorophore.

In some embodiments, quantitative detection can be performed by fluorescence microscopy quantification performed at each site of the microfluidic test matrix, and in particular with an approach described in [ref. 43].

In some embodiments, quantitative detection can be performed by chemi-luminescence, including, for example, labeling the top antibody in the sandwich immunoassay with a chemi-luminescent tag.

In some embodiments, quantitative detection can be performed by electrical detection, including, for example, labeling the top antibody in the sandwich immunoassay with an enzyme, which converts a neutral substrate into charged products, e.g. in a redox reaction. Then the increase in the available charge carriers will produce a local increase in the conductivity, which can easily be measured electronically to a very high sensitivity with high speed and parallelism of detection. Then the microfluidic matrix will be mimicked by an electrical detection matrix, e.g. built into the substrate of the chip.

In some embodiments, quantitative detection can be performed by photonic resonators, and in particular with the photonic resonator described in [ref. 10]. For example, in some of those embodiments, the microfluidic matrix can be mimicked by an array of photonic resonators, in such a way that there is a least one independently addressable photonic resonator detector in each of the microfluidic immunoassay chambers. Then the immunoassay can be formed on top of the resonator, whose optical properties will change as the sandwich immunoassay is completed (e.g. it can tune or detune as a result). Thus in some embodiments detection is performed by a reporting scheme that involves a photonic resonator measurement at each immunoassay chamber instead of a fluorescence measurement. In some embodiments, each photonic resonator can be combined with a nanolaser, or the nanolaser can be used instead of it. In some embodiments, each nanolaser's properties would change as a result of binding of the target.

Other reporting schemes are suitable in various embodiments herein described, and are identifiable by a skilled person upon reading of the present disclosure.

The output of the overall system can vary depending on application and choice of constituent stages. In particular, a diversity in the output is typically associated to the inherent modularity of the proposed methods/system.

For example, changing the reporting scheme will change the type of signal output received. For fluorescence and chemi-luminescence, the output would be a change in the intensity and/or spectrum of an optical signal. For photonic measurements, the output may be a change in intensity and/or spectrum of an optical signal. For electrical measurements, the result would be changes in the conductivity, capacitance, resistance, or throughput electrical current. For measurements with radioactive labels, the result can be chemical changes in the photographic plate, or photoelectric signal in an electronic detector.

In another embodiment, e.g. where the blood separation is the key, the output can be both an immunoassay signal and the filtration results themselves, e.g. if the system is required to output WBCs in addition to the quantification of particular analytes carried in the plasma.

In some embodiments, the overall system can be reduced to one or more of its constituent stages for very specific applications.

In some embodiments, the devices methods and system of the present disclosure provide a quantitative sensitivity limit at around 4 pM or higher.

In some embodiments, wherein there is a large dynamic range between the sensitivity limit (4 pM) and the "normal" value of a target (e.g. 96 pM for VGF), the devices methods and systems herein described can be used to quantify underexpression.

In some embodiments, the devices methods and system of the present disclosure are applicable to a broad range of clinical diagnostic tests that are based on quantifying proteins in human plasma.

In some embodiments, the devices methods and system of the present disclosure allow reduction in required sample volume and related new types of clinical and fundamental studies, e.g. a broad, multianalyte screening of a large number of small-volume samples from existing bio-banks organized by the respective symptomatic pathologies, e.g. multiple sclerosis, particular types of cancer, etc.

In some embodiments, the devices methods and system of the present disclosure have the inherent capability of multianalyte detection [refs. 43, 44], which is expected to cut costs, while the system would also use up only a small fraction of the precious banked sample.

In some embodiments, the devices methods and system of the present disclosure can be used in connection with routine biomedical diagnostics.

EXAMPLES

The devices, methods and systems herein described are further illustrated in the following examples, which are provided by way of illustration and are not intended to be limiting.

In particular, the following examples illustrate an exemplary device, methods and systems herein described with reference to detection of ferritin and VEGF. A person skilled in the art will appreciate the applicability of the features described in detail for detection of those biomarkers for additional biomarkers or targets in general according to the present disclosure.

Additional details concerning procedures used and results obtained are reported below.

Example 1

Mold and Chip Fabrication, Reagents, and Experimental Setup

Mold and chip fabrication and the experimental setup were performed as described in [ref 42] incorporated herein by reference in its entirety. Fresh resupplies of the same commercial reagents for the same companies were utilized. The size of the microfluidic chip was reduced to 60 chambers (6 sample coliseums crossed by 5 test lanes, with two chambers per sample-test combination), while the chamber size was allowed to vary among test lanes (FIG. 1).

In comparison to the chip described in [ref. 42], the microfluidic device was shrunk from 100 to 60 chambers (6 sample coliseums, 5 test lanes, 2 chambers per combination), since 6 datapoints per measurement were enough to produce a calibration of sufficient quality. This reduction would also make it easier to integrate the device as a subsystem in a future multi-antigen chip.

Figure 1B:
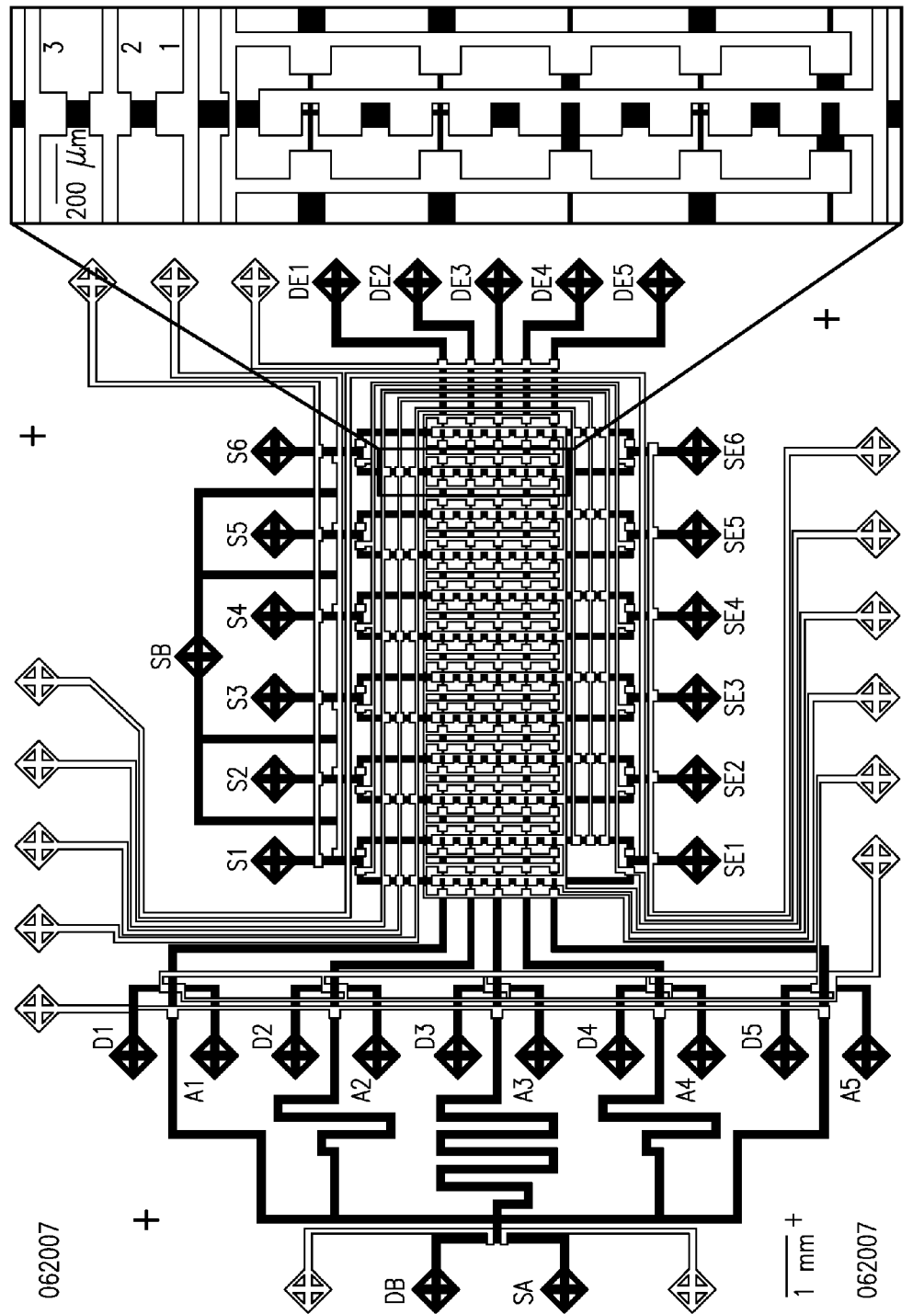
FIG. 1B shows an architectural diagram of a microfluidic chip according to some embodiments herein described. Control channels are depicted in grey, flow channels are depicted in black. The inset shows a schematic representation of an architectural diagram of a test column. Vertical and horizontal comb-like valve arrays enclose individual chambers.

Channel resistances of test lanes were made approximately equal by adding length to the most direct route from source to exhaust, as exemplified by the zigzags in Lanes 2, 3, and 4 (FIG. 1B). In addition, the lanes with smaller chambers were designed with wider channel segments connecting the chambers (FIG. 1B zoom-in), so that the total fluidic resistances of the matrix lanes were kept approximately the same. That feature helped avoid lane bias, as different lane resistances at the same pressure would have generated different throughputs and thus different dosimetry across the test matrix.

Figure 1C:
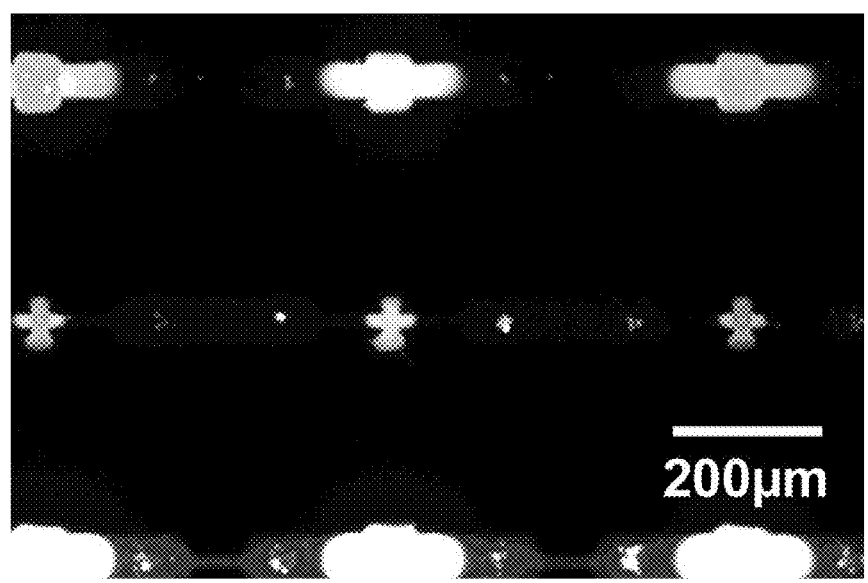
FIG. 1C shows a depiction of fluorescence immunoassay spots according to some embodiments here described. Strong fluorescence signal emanates from the capture chambers when the sought antigen is present in the sample and the immunoassay stacks are properly completed.

The sizes of the capture chambers were varied as an additional lever of control in configuring the dynamic range of the system. Intersection sizes of 20×20, 60×60, and 100×100 microns were utilized (FIGS. 1B and 1C). The hypothesis was that larger area would allow the capture of more analyte before reaching surface saturation, and thus would handle samples of high concentration of analyte, while smaller areas would concentrate a rare sample for high-sensitivity measurements. However, experimental observations showed that at the desired low antigen concentrations, the system seems roughly to scale the level of binding with the ambient concentration.

Thus, in the particular experimental settings tested, the size of the capture area did not prove as useful as anticipated according to the specific experimental design. This was not a surprising, as the system was operated far from saturation. Additional details are described in [ref. 44] incorporated herein by reference in its entirety.

Example 2

Determination of Fluorescence Noise

The potential increase in fluorescence noise due to the complexity of the sample analyzed, serum sample, e.g. through non-specific attachment of blood proteins and then fluorescence probes to the channel surfaces, was investigated.

Background/noise was estimated in two ways. First, a control measurement was included by feeding buffer with 0.1% BSA instead of a serum sample. So, there were: one buffer sample, one unspiked serum subsample, and four spiked serum subsamples, for a total of six coliseums. The control measurement quantifies the noise from non-specific attachment of labels or any cross-reactivity that may occur in the absence of serum. Second, each fluorescence image of a reaction chamber contains a local autofluorescence background from the material of the chip itself.

This second contribution to background/noise was estimated by measuring fluorescence signal from non-channel regions of the fluorescence image and then weighting it by the ratio of chamber area to non-channel area used to collect that autofluorescence signal. Thus the signal from each chamber was reduced by its local background, including the signal from the control chamber. Then the resulting signal for each serum chamber was reduced by the resulting signal from the control chamber, to produce the final net signal for each chamber. Since there are two chambers per sample-test combination, their average was taken as the net signal for the combination, while half of their difference was assigned as uncertainty on that net signal. These net signals with their uncertainties were plotted to produce the recalibration curve.

Example 3

Quantification Scheme

Detection of Ferritin was performed by sandwich immunoassay in the chip manufacture as illustrated in Example 1.

In sandwich immunoassays, a monoclonal antibody, specific to the target analyte (antigen), is bound to a surface. Next, the sample is put in contact with that surface, whereby the antibody captures the contained antigen. Then a labeled polyclonal antibody attaches to the antigen to complete the sandwich immunoassay. The label (e.g. a linked enzyme creating fluorescent product or a fluorophore bound to the polyclonal antibody) generates a signal which is compared to a standard to quantify the captured antigen.

The chips shown in the exemplary illustration of FIG. 1A multiplex this scheme to allow 5 simultaneous tests for each of 6 samples. Micromechanical valves direct the pressure-driven reagent flow as desired along a network of 10-µm-tall channels (FIG. 1B). The "four-way" valving at each intersection in the test matrix forms a capture microchamber, within which the sandwich immunoassay is built for a particular sample-test combination. FIG. 1C shows a section of the array of the sandwich immunoassay fluorescence spots generated in a typical experiment.

In a typical experiment, monoclonal antibodies flow from D1-5 (Derivatization inputs) to DE1-5 (Derivatization Exhausts) in FIG. 1B. The antibodies covalently bond to the epoxide floor of the microchannels, producing the first layer of the sandwich immunoassay. Tris buffer from DB (Derivatization Buffer input) to DE1-5 removes unbound excess protein and passivates any unreacted epoxide moieties that would otherwise produce background by binding protein in later feeds. Next, Tris buffer flows from SB (Samples' Buffer input) to SE1-6 (Samples' Exhausts) to passivate the rest of the microchannels.

As samples flow in parallel from S1-6 (Samples' inputs) to SE1-6, each sample fills a corresponding pair of microchannels. When the appropriate valves are closed, each such pair forms a circular path (a coliseum), which traps 10 mL of the respective sample. Then an array of peristaltic micropumps, such as the one shown in [ref. 44], drives each trapped volume around its coliseum (see e.g. flow mechanism described in [ref. 42]), with a lap time of 20 sec. Within each coliseum, each antigen is captured in its respective microchamber, as determined by the first layer of the immunostack. The same sample is allowed to run multiple laps to maximize extraction of the antigen from the sample.

After harvesting, buffer from SB to SE1-6 flushes out the sample volume. Parallel feeds of biotinylated antibodies from A1-5 (Antibody inputs) to DE1-5 build up the third layers of the immunostacks in each microchamber. Buffer from DB to DE1-5 removes unattached antibody. Fluorescently labeled streptavidin in PBS buffer flows from SA (StreptAvidin input) to DE1-5. Buffer from DB to DE1-5 removes unattached excess. Then all valves are closed and fluorescence detection is conducted at each microchamber using an inverted optical microscope and an inexpensive cooled CCD camera. The fluorescence signal is integrated over the chamber area and then lessened by the off-channel background signal normalized for area, to produce the net fluorescence signal from the immunoassay spot. That result is correlated with the fed analyte concentration (see e.g. correlation described in [ref. 42]).

In human serum measurements, this basic scheme was further improved. To account for potential biological peculiarities or differences among patients, the human serum sample to be used for testing the microfluidic system was produced by mixing serum samples from ten randomly chosen anonymized patients and then quantifying the analytes of interest by standard clinical means.

Next, instead of having multiple samples in the same chip, the compound serum sample was aliquoted and each aliquot was spiked with varying known concentrations of a commercially available antigen equivalent to the indigenous human analyte to be detected. These derivative samples were then fed into the chip in parallel and together with a negative control sample containing PBS buffer with 0.1% BSA.

Then fluorescence signals from each image were obtained as described above. The values for the serum samples were then lessened by the negative-control value, to subtract the contribution from potential non-specific attachment. The resulting net fluorescence signals were plotted as a function of spike concentration to produce a calibration curve. Under suitably chosen feed conditions that curve would be close to a straight line (see e.g. Example 4 and Example 8). The zero-spike value was divided by the slope of the linear fit to yield the indigenous analyte concentration.

Example 4

Ferritin Quantitative Detection in Blood

Figure 2:
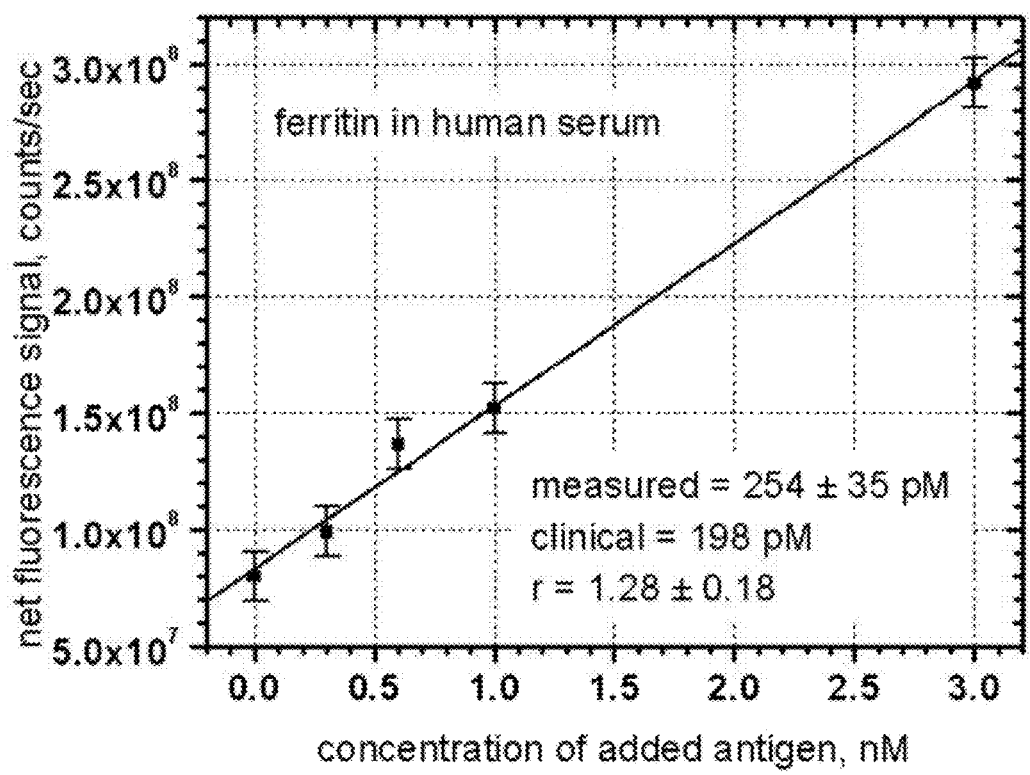
FIG. 2 shows a diagram illustrating calibrations in human serum according to some embodiments herein described. The X axis reports the net fluorescence signal detected following a sandwich immunoassay. The Y axis reports the concentration of added antigen analog in each subsample.

A particular example of a ferritin calibration result is shown in FIG. 2. Of the six available coliseums, one was used for a negative control (PBS buffer, 0.1% BSA [ref. 42]) to estimate non-specific attachment, one was used with pure (unspiked) serum, and the other four with the same serum but spiked to respective concentrations of 0.3, 0.6, 1, and 3 nM of commercially available antigen. The specifics of this experiment included two capture cycles, each comprising a 30-sec sample feed and a 5-min circular pumping. A fluorescence image of each capture chamber was taken with a 4-sec photoexposure.

Spiking the human serum sample with known concentrations of a commercially available antigen analog and measuring all resulting aliquots produces the calibration curve illustrated in FIG. 2.

In particular, the net signal was extracted from the fluorescence image of the respective immunoassay chamber with a procedure substantially similar to the one described in Example 3.

Briefly, the glass substrate of the device is essentially transparent in visible frequencies, so fluorescence measurements can be conducted from the bottom side of the device. An inverted fluorescence microscope was used for the purpose. Since each sample-test combination has its own distinct chamber on the chip, multi-color experiments are not necessary for quantification, because the location provides the sample-test knowledge, while the magnitude of the signal correlates with the amount of captured analyte. In the particular embodiment, we used a mercury lamp for illumination, an inverted Olympus microscope, a dichroic filter set for AlexaFluor488, and a cooled CCD camera. The antibodies were labeled with biotin, while streptavidin labeled with AlexaFluor488 fluorescent dye was fed to each chamber as part of the experimental procedure. Bound antibodies had their biotin tag immobilize streptavidin, whose fluorescent tag produced the fluorescence signal. A fluorescence image was taken with the CCD camera at each chamber. FIG. 1C below shows several chambers at the same time as an illustration of the results of the technique, but for purposes of data collection, each chamber was imaged separately with a higher-magnification objective. Each such picture contained the channel crossing and some background areas without channels. In each image, the background areas were used to estimate the fluorescence background, which was then subtracted from the fluorescence signal integrated over the chamber. The result was a net fluorescence signal from each chamber. Those data were then organized by spiking concentration and plotted. A linear fit to the resulting curve produces a slope. Then the zero-spike signal is divided by the slope to calculate the endogenous concentration of the analyte. The described system is geared for fluorescence detection. However, different labeling schemes, e.g. as described above, would require their own respective detection methods and hardware.

The net signals for each spiking concentration (including zero-spike) were then plotted on the same graph as a function of the spiking concentration (FIG. 2). Uncertainties are assigned based on standard error propagation using the calculations involved in the image analysis technique and the uncertainties of the starting variables. For example, one source of uncertainty is the human error involved in boxing the chamber single for purposes of integration. Another source of error is the selection of background window for weighted subtraction, to obtain the net signal. Yet another source of uncertainty is the variation between the values of the two chambers that by construction would produce identical results (since in the particular experimental settings chosen, each antibody channel intersects the same coliseum at two locations).

A linear fit in the graph of net signal vs. spiking concentration produces a value for the slope, with associated uncertainty (FIG. 2). Then the zero-spike net signal is divided by the slope, to obtain the endogenous concentration. Standard error propagation is applied on the uncertainties on slope value and zero-spike value to calculate the uncertainty on the estimate of the endogenous concentration.

The values for spiking concentrations were selected to cover the expected dynamic range of the analyte while bearing in mind its "normal" concentration and direction of abnormal change. For example, ferritin's typical range in serum is 60-600 pM, with sizeable overexpression serving as an indication of long-term iron buildup. So, allowing for overexpression, a spiking range was selected of 300-3000 pM for the experiment, whose results are shown in FIG. 2. Conversely, in experimental design where underexpression is desired (e.g. as the medically indicative result), a spiking range few times below the "normal" (or other preselected level) and then at the high end be at the "normal" level or slightly above. The obvious intention is to cover the expected dynamic range of the particular analyte. If the analyte's expression level does not vary significantly, a linear scale in the spiking is appropriate (e.g. 200, 400, 600, 800 pM). If the expression level varies significantly, e.g. by a few times or even an order of magnitude or more, a logarithmic scale for the spiking is more appropriate (e.g. 3, 10, 33, 100, 333, 1000 pM).

The resulting calibration curve (FIG. 2) was used to estimate the indigenous ferritin concentration.

The indigenous concentration of the analyte of interest is calculated from the slope of the linear fit and the zero-spike value. The shown example is for ferritin, where the chip result was 254±35 pM, while the clinically measured value was 198 pM.

By comparison, the independent clinical measurement (obtained through Roche Elecsys 2010 in the USC Reference Laboratory) had yielded 198 pM for the same serum sample. Thus in this case, our microfluidic device measured 28% higher concentration than the commercial macro system.

Figure 3A:
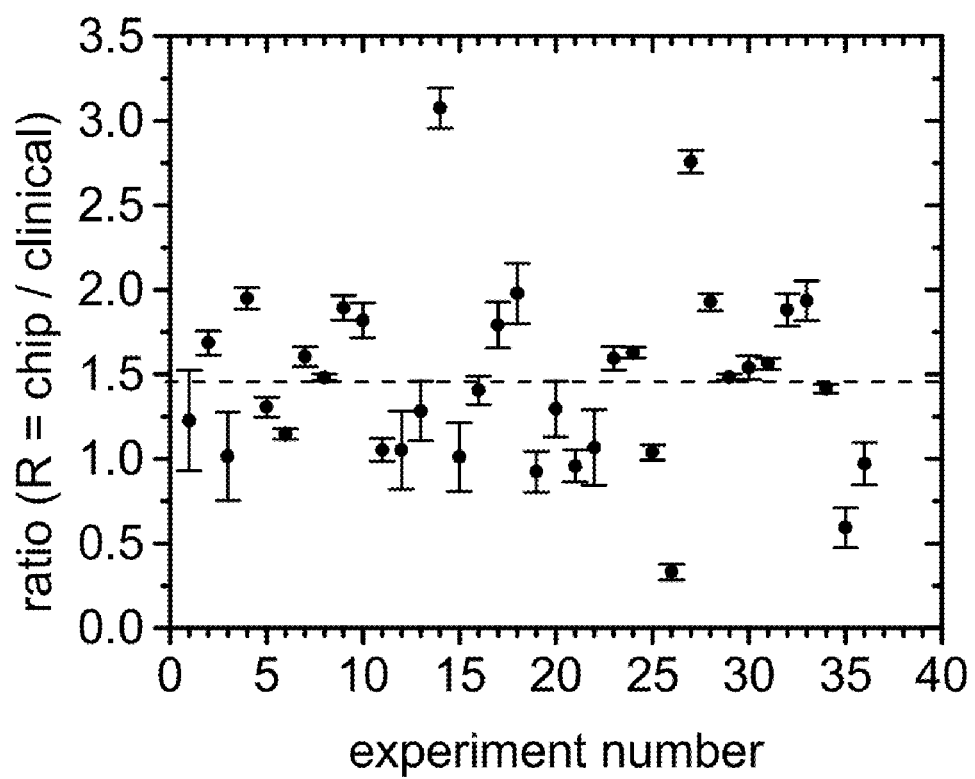
FIG. 3A shows instrumental statistics related to devices methods and systems according to some embodiments of the present disclosure. The y axis reports the ratio between the values detected in a chip and according to clinical determination and the x axis reports the experiment numbers. The results of 36 analogous measurements of ferritin in the same human serum sample are presented as a scatter plot.
Figure 3B:
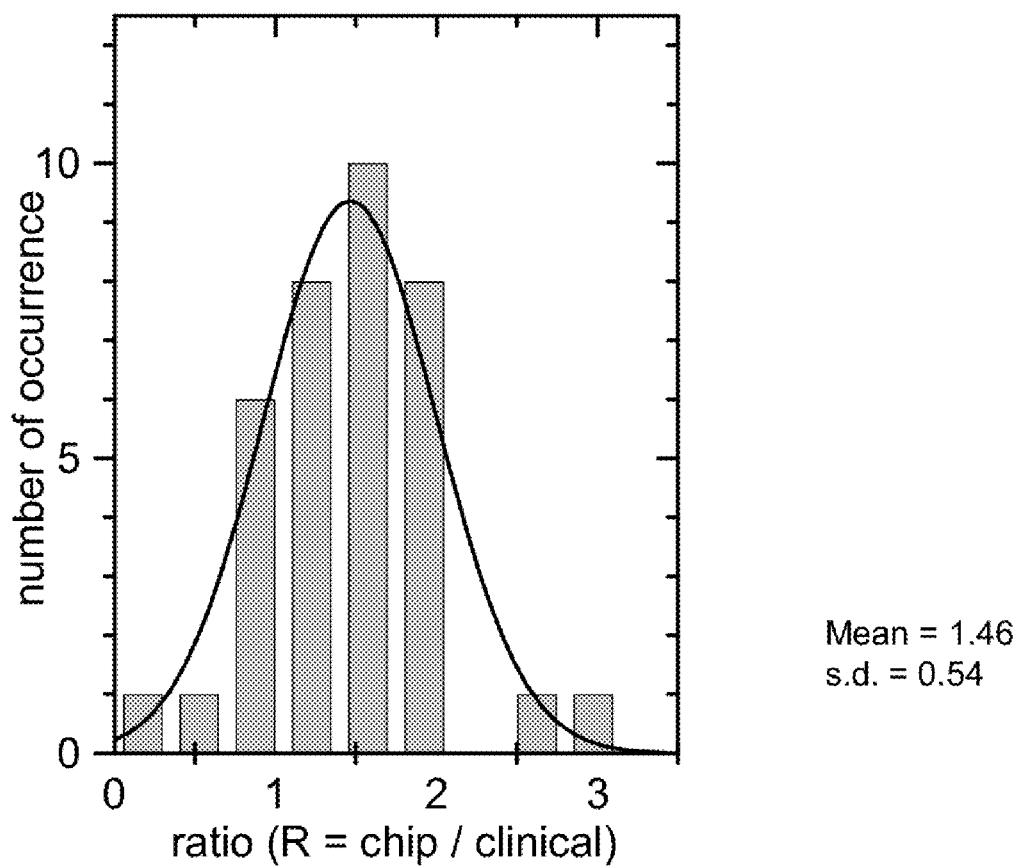
FIG. 3B shows instrumental statistics related to devices methods and systems according to some embodiments of the present disclosure. The x axis reports the ratio between the values detected in a chip and according to clinical determination and the y axis reports the number of occurrence. In particular, the results of 36 analogous measurements of ferritin in the same human serum sample are presented as a histogram.

36 analogous measurements on the same serum sample were conducted to validate the system and determine the degree of reliability and reproducibility of the obtained results. For each serum measurement, the estimated value of ferritin concentration was divided by the clinically measured value to produce a ratio parameter R. FIG. 3A presents the compiled data as a scatter plot of the values of R for the 36 experiments conducted. FIG. 3B presents the same data in the form of a histogram. A normal fit to the histogram distribution yielded a mean of 1.46 with a standard deviation of 0.54.

No visible difference or systematic clustering among subsets of measurements was observed. The results showed agreement and reproducibility across different test lanes in the same device as well as across different devices, thereby demonstrating the overall reproducibility and reliability of the system. The chief contributor to the observed quality was attributed to the in-built calibration scheme which nullifies drift factors such as variations in reagent activity, surface chemistry quality, and fabricational conditions.

Example 5

Device Fabrication

The Flow layer mold was manufactured according to the following procedure. 3-Inch silicon wafers were treated with hexadimethylsilazane (HDMS) vapors for 3 min. SPR 220-7 photoresist (MicroChem Corp. Newton, Mass.) was spun onto the wafer using aWS-400A-GNPP/LITE spincoater (Laurell Technologies, North Wales, Pa.). The wafer was baked at 105° C. for 90 s, UV-exposed through a printed transparency mask at a Karl Suss MJB3 mask aligner, and developed in SPR 220-7 developer. The mold was baked on a hotplate at 140° C. for 30 min with ramping up from and back to room temperature.

The control layer mold was manufactured according to the following procedure .SU8-2010 (MicroChem Corp, Newton, Mass.) was spun onto 3-inch silicon wafer using the same spin coater. Pre-exposure bake was 2 min at 65° C., then 6 min at 95° C. UV exposure was done at the same mask aligner for 1.75 min. Post-exposure bake was 2 min at 65° C., then 6 min at 95° C. The mold was developed in SU8 developer (MicroChem Corp, Newton, Mass.).

The elastomer chip was then manufactured as follows. Molds were exposed to tetramethylchlorosilane (TMCS) vapors for 3 min. Then 35 and 21 g of PDMS pre-polymer, in monomer-to-catalyst weight ratio of 5:1 and 20:1 respectively, were stirred and degassing using a HM-501 hybrid mixer (Keyence, Long Beach, Calif., USA). The 20:1 mixture was spun onto the flow layer mold at 1500 rpm for 60 s using a P6700 spincoater (Specialty Coating Systems, Indianapolis, Ind., USA). The 5:1 was poured directly onto the control layer wafer. Both were baked in an 80° C. oven for 30 min.

The control layer was peeled off the mold and cut out into devices. Control ports were punched using a 20-gauge Intramedic TM Luer-Stub adapter (BD Biosciences, Franklin Lakes, N.J.). The devices were then aligned and assembled to the flow layer under a stereoscope.

The result was baked in an 80° C. oven for 1 h. Devices were cut out and peeled off the flow layer mold. Ports for the flow channels were then punched using the same 20-gauge adapter. The resulting PDMS chips was washed in ethanol, dried with nitrogen, and attached to epoxide-coated glass slides (Arrayit Corporation, Sunnyvale, Calif.). A final 12 h bake was performed to bond the PDMS chip to the slide.

Example 6

Sample Preparation

A compound human plasma sample was produced at the USC Reference Lab by combining the leftover plasma samples from six anonymized patients. A portion of the compound sample was sent to Quest Diagnostics Nichols Institute (San Juan Capistrano, Calif.) for VEGF quantification by conventional clinical means. The returned result was 42 pg/mL. The rest of the sample was aliquoted and frozen at −20° C. for storage.

For each on-chip experiment, an aliquot would be thawed and split into five samples. Four of them would be spiked with a different concentration of antigen that was a commercial analog to the analyte of interest. The fifth one would remain unspiked. The resulting preparations were fed as separate samples on the same chip, along with a sixth sample (Tris 1×, 0.1% BSA) for control.

Example 7

Experimental Set Up and Procedures

The microfluidic fluorescence microscopy station contains an inverted Olympus IX-71 fluorescence microscope (Olympus America, Melville, N.Y.) equipped with a mercury lamp (HBO® 103 W/2; OSRAM Munich, Germany) and a cooled CCD camera ST-7I (Santa Barbara Instrument Group, Santa Barbara, Calif.). Microfluidic control is provided by 8CM solenoid valve arrays and a BOB3 box (Fluidigm Corp., San Francisco, Calif.) directed by a PCI NI-DAQ card from National Instruments.

23-Gauge steel tubes (New England Small Tube, Litchfield, N.H.) are inserted into the control and flow layer ports of the chip (FIG. 1A). (As the diameter of the ports is smaller than the outer diameter of the tubes, the chip material is stretched around the tubes and holds them snugly. The resulting seal typically remains airtight up to 25 psi pressure difference.) The control layer is filled with water using Tygon® tubing (Cole-Parmer, Vernon Hills, Ill.) connected to the 8CM arrays. The flow layer is filled with samples and reagents through Tygon® tubing connected to pressure manifolds from Corning. The operating air pressures are maintained at 13 psi for control channels and 8 psi for sample and reagents channels, using regulators from AirTrol.

The chip (FIG. 1A) is essentially a two-dimensional matrix of analyte capture chambers with added input/output ports for samples, reagents, and pneumatic control. The chambers are formed at the intersections of reagent and sample channels (in black). The chambers can be isolated from one another by a vertical and a horizontal array of pneumatic microvalves operated through control channels (in gray). During each feed, valves are opened or closed to form a fluidic pathway from input to exhaust for only the desired sample or reagent.

Example 8

VEGF Quantitative Detection

In a quantification experiment, VEGF monoclonal antibody (R&D Systems, Inc., Minneapolis, Minn.) is fed from inputs D1-5 to exhausts DE1-5 (FIG. 1B) in 10 cycles of 60-s flow and 60-s incubation. The monoclonal antibody travels along the 5 test lanes (horizontally to the right in FIG. 1B) and bonds covalently to the epoxide-coated glass substrate, which forms the floor of the reagent channels. Next, buffer (Tris 1× (Sigma-Aldrich), 0.1% BSA) is fed from input DB to exhausts DE1-5, to flush the non-bound monoclonal antibodies out of the test lanes and to passivate any unreacted epoxide.

Buffer of the same content is then fed from input SB to exhausts SE1-6 vertically downward in FIG. 1B, to passivate the epoxide along the sample paths as well. The passivation feeds also ensure that BSA blocks non-specific-binding sites on the elastomer channels walls, which otherwise might later bind fluorescently labeled streptavidin and produce false signal during detection and quantification. Low signal from controls attests to the success of the technique.

Similarly to what already discussed with reference to ferritin detection, also for VEGF, the values for spiking concentrations were selected to cover the expected dynamic range of the analyte while bearing in mind its "normal" concentration and direction of abnormal change. VEGF's "normal" level is around 96 pM in plasma, while overexpression is an indication of cancer. So, allowing for overexpression, a spiking range of 30-1000 pM for this experiment were used.

Spiked plasma subsamples were then fed from inputs S1-5 to exhausts SE1-5, while buffer (Tris 1×, 0.1% BSA) is simultaneously fed from S6 to SE6 as a control, in 10 cycles of 60-s flow and 60-s incubation. During each incubation, the subsamples are pumped along respective circular paths (coliseums [refs. 43, 44], FIG. 1B) using an array of peristaltic pumps set at a 3-s cycle. This technique ensures that the same plasma passes over the capture sites multiple times, thereby maximizing the capture of analyte by the immobilized antibody.

After the plasma feeds, buffer (Tris 1×, 0.1% BSA) from SB to SE1-6 flushes out the remaining plasma. Biotinylated VEGF polyclonal antibody (R&D Systems, Inc., Minneapolis, Minn.) is fed from inputs A1-5 to exhausts DE1-5 in 10 cycles of 60-s flow and 60-s incubation. The antibody attaches to the captured analyte and completes the sandwich immunoassay. Buffer (Tris 1×, 0.1% BSA) is then fed from input DB to exhausts DE1-5 to flush unbound antibody.

Streptavidin tagged with Alexa Fluor 555 (Invitrogen Corp., Carlsbad, Calif.) is fed from input SA to exhausts SE1-5 in 10 cycles of 60-s flow and 60-s incubation. The streptavidin binds to the immobilized biotinylated antibody. Buffer (Tris 1×, 0.1% BSA) is fed from DB to DE1-5 for 10 min to flush the excess streptavidin. The CCD camera is cooled to −5° C. and a fluorescence image is taken of each capture chamber in the matrix with a 5-s exposure.

Figure 4:
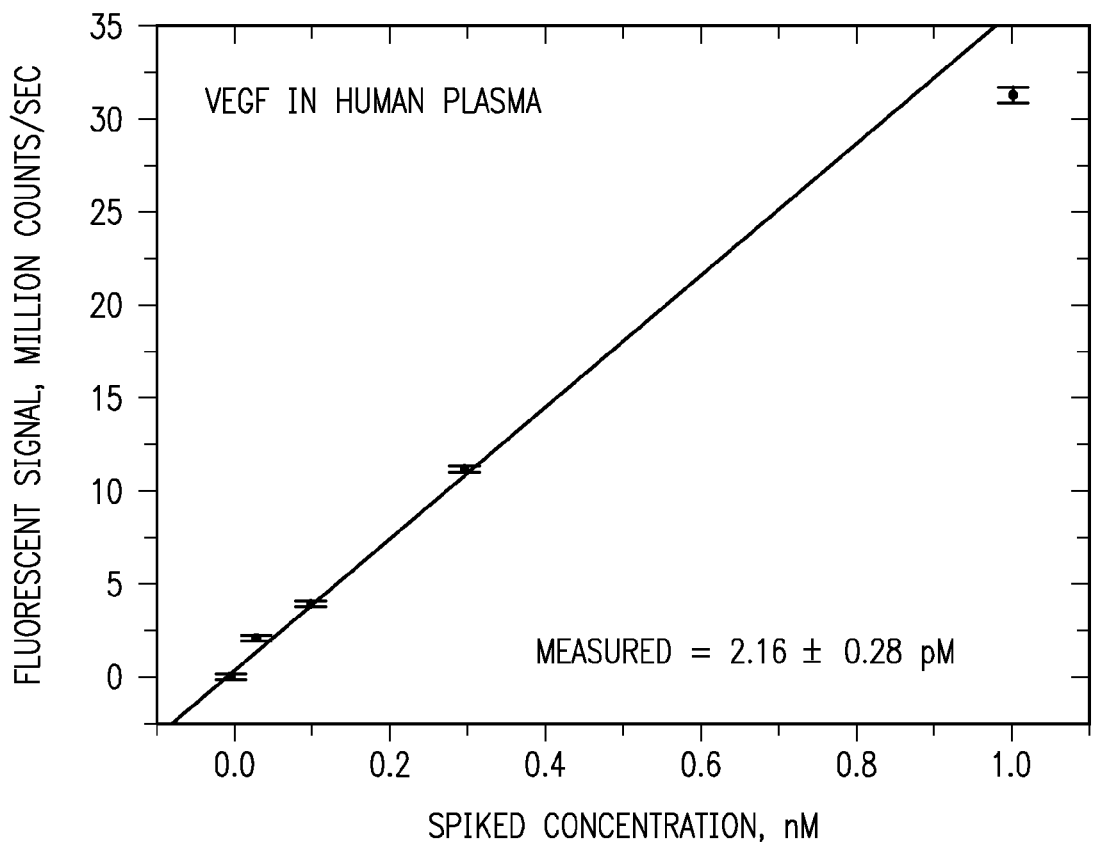
FIG. 4 shows quantification of VEGF in human plasma according to some embodiments herein described. The plasma sample was spiked with known concentrations of commercially available analog.

Signal quantification inside fluorescence images was done by drawing boxes in Astra Image and using the inbuilt summation function. The net signal for each image was calculated as the chamber signal diminished by the background signal adjusted by a factor equal to the ratio of the boxed chamber area to the boxed background area. All the net signals from plasma chambers were diminished by the net signal from the respective control chambers along the same test lane in the device. The results were then plotted as a function of spiked concentration. A linear fit (R=0.9757, p=0.0045) was produced to obtain the slope of this calibration curve (FIG. 4). Dividing the zero-spike signal by the slope produced the endogenous concentration of the analyte.

The endogenous VEGF concentration is calculated from the slope of the linear fit and the zero-spike net signal. Here, the linear fit (R=0.9757, p=0.0045) indicated a concentration of 2.16±0.28 pM, while the clinical result was 1.6 pM.

Figure 5A:
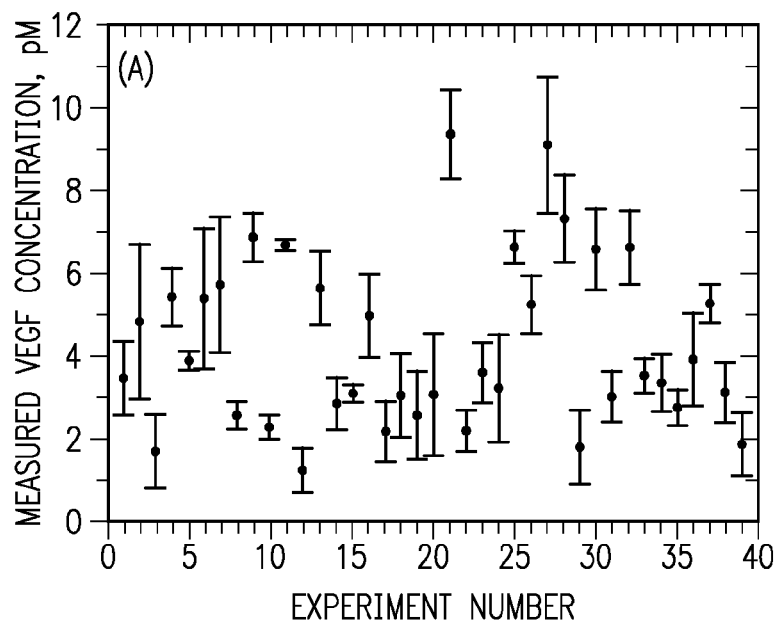
FIG. 5A shows a diagram illustrating instrumental performance according to some embodiments herein described. In particular, the results of 39 analogous measurements of VEGF in the same human plasma sample are presented as a scatter plot. The x axis reports the experiment number and the y axis reports the VEGF concentration detected according to some embodiments herein described.
Figure 5B:
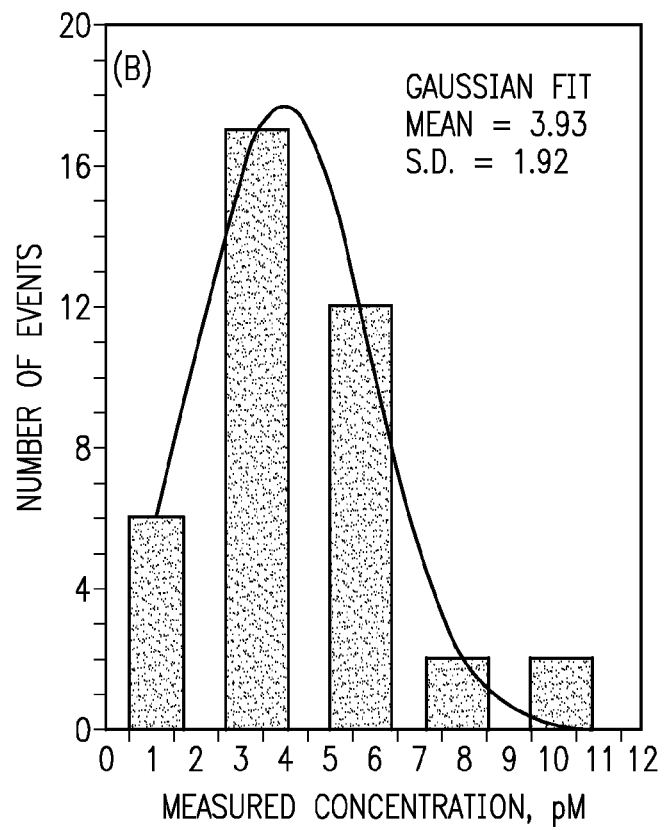
FIG. 5B shows a diagram illustrating instrumental performance according to some embodiments herein described. In particular, the results of 39 analogous measurements of VEGF in the same human plasma sample are presented as a histogram. The x axis reports the VEGF concentration measured according to some embodiments herein described and the y axis reports the number of events.

Results from the multiple quantitations of the same compound plasma sample were organized in a scatter plot (FIG. 5A) and a histogram (FIG. 5B).

No systematic clustering among subsets of measurements was observed. The results showed agreement and reproducibility across different test lanes in the same chip as well as across different chips, thereby attesting to the overall reproducibility of the results.

A proof of principle was set out for the use of our multi-analyte microfluidic fluorescence immunoassays system [refs. 43, 44] with human plasma. For this purpose, VEGF was chosen as the analyte to quantify, due to its significance as a cancer biomarker, its low typical endogenous concentration (2,500 pg/mL, 96 pM "normally"), and the standing practice of quantifying it in human plasma.

An in-built recalibration scheme was utilized such as the one described in Example 3.

In particular, in human serum measurements, to account for potential biological peculiarities or differences among patients, the human serum sample to be used for testing the microfluidic system was produced by mixing serum samples from ten randomly chosen anonymized patients and then quantifying the analytes of interest by standard clinical means.

Next, instead of having multiple samples in the same chip, the compound serum sample was aliquoted and each aliquot was spiked with varying known concentrations of a commercially available antigen equivalent to the indigenous human analyte to be detected. These derivative samples were then fed into the chip in parallel and together with a negative control sample containing PBS buffer with 0.1% BSA.

Then fluorescence signals from each image were obtained as described above. The values for the serum samples were then lessened by the negative-control value, to subtract the contribution from potential non-specific attachment. The resulting net fluorescence signals were plotted as a function of spike concentration to produce a calibration curve. Under suitably chosen feed conditions that curve would be close to a straight line (FIG. 2). The zero-spike value was divided by the slope of the linear fit to yield the indigenous analyte concentration.

In each experiment, an aliquot of a human plasma stock was split into five samples, four of which were spiked with a different concentration of commercial antigen analog, while the fifth was left pure (unspiked). A buffer control was also included as a sixth sample to offer an estimate of the noise. These samples were processed on the chip. A calibration curve (e.g. FIG. 4) was plotted for the net fluorescent signal from the plasma samples as a function of the spiking concentration. The net signal from the pure (zero-spike) plasma sample was divided by the slope of the linear fit to the calibration curve, to obtain a measurement of the endogenous analyte concentration.

Each chip (FIG. 1A) produced up to five independent measurements of VEGF in the same plasma aliquot, since the microfluidic matrix (FIG. 1B) contains five independent test lanes. Results from multiple measurements within the same chip were combined with results from other chips to produce a scatter plot (FIG. 3A) and a histogram (FIG. 5B). A Gaussian fit to the histogram produced a mean of 3.93 pM and a standard deviation of 1.92 pM, while the clinical Quest Diagnostics measurement of the same sample produced a value of 1.6 pM (42 pg/mL). A likely explanation for that discrepancy that is not intended to be limiting and is provided herein for the purpose of guidance only, is that the discrepancy indicates the limit of quantitative sensitivity of the system under the settings used. Thus the results indicate that the system works correctly down to a concentration of a few pM for the target VEGF with the specific experimental settings here described.

No visible difference or systematic clustering among subsets of those measurements. The results showed agreement and reproducibility across different test lanes in the same device as well as across different devices, thereby demonstrating the overall reproducibility of the system. Also in this case chief contributor to the observed quality was the in-built recalibration scheme.

The self-consistence of the results obtainable over a significant number of independent measurements (N=39) support observation of a real phenomenon. The observed the results obtained by standard clinical measurements and by our chips was 1.6 pM and 3.93±1.92 pM respectively.

Additionally, based on these results, the system herein described is immediately usable for VEGF quantification in human plasma, since VEGF is usually overexpressed in practice. In addition, there is a large dynamic range between our sensitivity limit (4 pM) and the "normal" value (96 pM), in which the system can quantify underexpression, e.g. brought about by VEGF-reducing anticancer drugs [refs. 45,46].

Additional details on the calibration scheme are described in [ref. 44] incorporated herein by reference in its entirety Example 9

Quantitative Detection of Blood Proteins

The serum technique described in the examples above were used to quantify the endogenous concentrations of ferritin, prostate specific antigen (PSA), thyroglobulin, c-reactive protein (CRP), and vascular endothelial growth factor (VEGF), within the compound human serum sample. In particular, the experimental procedures illustrated in the preceding examples Table 1 shows a comparison among the above mentioned analytes an analytes that are typically measured in standard blood tests.

TABLE 1

| protein | conc | ml | indication | time | kDa | #/nL | conc, M |
|---|---|---|---|---|---|---|---|
| Albumin | 3.5-7.5 g/dL | 7 | normal range | 4 hours | 66 | 5.50E+11 | 9.14E-04 |
| C3 complement | 70-150 mg/dL | 7 | normal range | 4 days | 174 | 3.80E+09 | 6.31E-06 |
| Ceruloplsmin | 21-50 mg/dL | 5 | normal range | 36 hours | 132 | 1.60E+09 | 2.68E-06 |
| beta2 Microglobulin | >2.0 mg/L | 7 | is abnormal | 1 day | 11.8 | 1.00E+08 | 1.66E-07 |
| Thyroxine (T4) | 5-12 ug/dL | 7 | normal range | 72 hours | 777 | 6.60E+07 | 1.10E-07 |
| C-reactive protein | <1.2 mg/dL | 5 | is abnormal | 4 hours | 114 | 6.60E+07 | 1.10E-07 |
| Ferritin | 30-300 ng/mL | 7 | male range | 72 hours | 474 | 2.10E+05 | 3.49E-10 |
| AFP | >20 ng/mL | 7 | is abnormal | 96 hours | 70 | 1.70E+05 | 2.82E-10 |
| PSA | >4.0 ng/mL | 7 | is abnormal | 96 hours | 30 | 8.00E+04 | 1.33E-10 |
| VEGF | 2500 pg/mL | vary | plasma normal | days | 26 | 5.80E+04 | 9.60E-11 |
| Creatin Kinase MB | >5.0 ng/mL | 7 | indicates infarct | 4 hours | 84 | 3.60E+04 | 5.98E-11 |
| Thyroglobulin | 5-50 ng/mL | 5 | normal range | 7 days | 670 | 2.50E+04 | 4.15E-11 |
| CEA | >3.0 ng/mL | 7 | is abnormal | 72 hours | 180 | 1.00E+04 | 1.66E-11 |
| Calcitonin | >40 pg/mL | 5 | is abnormal | 4 days | 3,500 | 6.80E+03 | 1.13E-11 |
| Vasopressin | 2-12 pg/mL | 10 | plasma normal | 7 days | 1,084 | 3.30E+03 | 5.48E-12 |

In particular, Table 1 illustrates the required amounts of sample (several milliliters), the turnover time (days) and the typical concentration ranges. In Table 1 the selected analytes are indicated in gray shaded lines to emphasize comparison with other analytes.

In the experimental setting adopted, the best results were obtained with CRP and ferritin, most likely because their medically "normal" concentrations are highest among the selected analytes (1.2 mg/dL, 110 nM for CRP; 30-300 ng/mL, 350-3500 pM for ferritin).

VEGF (2500 pg/mL, 96 pM "normally") and PSA (4 ng/mL, 130 pM for a "normal" male) produced measurable signals in serum; however, the related uncertainties were high and thus produced low-quality fits so that the final results had large uncertainties as well with this experimental settings. However, adjustments of the experimental settings, focused on various experimental parameters (particularly feed time, pump time, and number of capture cycles) are expected to significantly improve those results.

Thyroglobulin ("normal range" of 5-50 ng/mL or 42-420 pM) appeared essentially undetectable in serum in this experimental setting even at very high spiked concentrations, supporting the conclusion that failure of detection was to be ascribed to the particular antibodies used in the specific experimental setting.

In view of the above, ferritin was selected for further tests, since (among the chosen five analytes) ferritin had the lowest indigenous concentration that could still be quantified reliably with the available antibodies in the specific experimental settings. A series of experiments was conducted to optimize the experimental parameters (e.g. feed pressure, feed duration, pump duration and frequency, spike concentrations, photoexposure) to adjust the dynamic range of the system so that the calibration curves were as close to linear as possible In view of the above results, it was possible to conclude a demonstrated capability of the system to measure analytes at indigenous concentration as low as 250 pM in human serum. Such sensitivity is adequate for many analytes in medical practice today.

The observed difference between the measured absolute clinical and chip values (FIG. 3) is very intriguing. One possible explanation herein provided for guidance purpose only and with no intention of being limiting is that since standard technology is at the macroscale, it is possible that the resultant diffusion limitations lead to an underestimation of the absolute amount of present analyte in standard clinical measurements.

In medical practice, "normal" values are obtained by statistics on the same type of measurement done in the same way on a very large number of patients. The resulting distribution yields confidence intervals which are then used to define "the normal value". Subsequently, any clinically measured value is compared to the "normal". That comparison determines if the analyte is over-expressed or under-expressed in the particular patient, who is then diagnosed accordingly.

Consequently, in biomedical measurements, metrological consistency and precision are far more important than the accuracy of the absolute value. In fact, there would be no practical difference so long as all measurements are "inaccurate in a consistent way". From that perspective, the mean value offset we observe is inconsequential in practical terms. Hence, in principle our system is immediately usable with the old tables of "normal values", by a simple arithmetic adjustment.

Thus, the critical parameter in judging the quality of the system herein described is the consistency of measurements, as quantified by the standard deviation of the histogram fit. A standard deviation of 107 pM (0.54×198 pM) sounds quite usable as the "normal" clinical ferritin range is 350-3500 pM. In addition, the deviation was extracted from a distribution of 36 measurements, while it is a reasonable expectation that a much larger number of measurements would have a smaller deviation still. Therefore, the true precision of the system is likely far better.

In comparison with other miniaturized devices, the system herein described is one of the few to have the demonstrated capability to work with realistic biomedical samples. While it is prudent and useful to test and debug emerging systems with buffer solutions as a preliminary step, the true and ultimate challenge is to produce meaningful results with real biosamples such as human serum, plasma, cerebrospinal fluid, urine, saliva, etc. With that requirement in place, the selection of demonstrated devices becomes far more limited [refs. 11, 21, 22, 25, 28, 29, 32, 36-38, 40]. In some embodiments, devices methods and systems herein described are the apparent leader with quantitative sensitivity to as low as 250 pM antigen in human serum, with one quantitative exception utilizing surface plasmon resonance (SPR) [ref. 25]. However, SPR is expensive and difficult to parallelize and miniaturize.

In some embodiments, the methods devices and systems herein described can also provide a significant improvement over the current large expensive macrofluidic robotic systems in clinical practice, as the chips herein described according to several embodiments can be disposable and use 1,000 times smaller samples (100s of nanoliter instead of 100s of microliter). In some embodiments, devices herein described can form the core of affordable decentralized portable systems for point-of-care diagnostics, which can replace phlebotomy with fingerpricks, make tests more accessible to pediatric patients, significantly speed up the test turnover time, and decrease overall medical costs [ref. 2]. The in-built calibration is an additional major advantage, as it eliminates certain sources of error and thus makes the results more reliable.

The maturity of microfluidic technology [ref. 43] fundamentally allows for reliable operation of such devices, which can and do accommodate the necessary functionalities and its respective architectures. More specifically, in some embodiments herein described, each immunoassay measurement under our scheme requires six subsamples. These are currently prepared off-chip but in a future embodiment can and will be split and spiked on-chip to pre-determined concentrations through microfluidic metering [ref. 45]. The additional complexity would not lead to undue increase in real estate, especially nowadays with the advent of microfluidic vias [ref. 46].

The engineering of the overall system and the low cost per device combine to offer the very important advantage of disposability. Disposability circumvents a host of problems, such as carryover contamination, cross-patient errors, biohazard issues, and maintenance downtimes due to sequential processing [ref. 2]. Getting ready for a new measurement is as simple as discarding one chip and replacing it with a new one within the same control and detection unit. In some embodiments, this architecture is optimal in terms of cost and performance, and thus stands the best chance of adoption in biomedical practice.

Adoption of devices methods and systems herein described in biomedical practice and in other applications can be further facilitated by overall system miniaturization, miniaturized on-chip pressure actuation, as well as a miniaturized detection system to replace the currently used fluorescence microscope.

Example 10

On Chip Aliquoting and Spiking Methods

In some embodiments, the aliquoting/splitting of the sample and spiking for the recalibration scheme can be performed on-chip.

In one embodiment, solutions of analyte can be mixed with portions of the sample by use of a technique known as "microfluidic metering" [ref. 53]. Within that technique, one way to meter the fluid is to know the fluidic throughput at particular device settings, and then control the length of time over which a certain channel supplies fluid into the mix. Another way to meter the desired volume is to have a mixing circle, in which sections of hardwired volumetric ratios are filled with the constituents for the desired mixture. Both these methods are known. According to the present disclosure the integration of these techniques with immunoassay chips can be performed for implementation of the recalibration scheme herein described.

In another embodiment, instead of liquid mixing, the analogs can be deposited in lyophilized form along the fluidic path of the subsamples, while the aliquoting is performed by simply splitting the channels. The subsamples re-suspend the analogs and move to the subsequent stages of the overall system. A schematic illustration of this approach is shown in FIG. 6.

Figure 6:
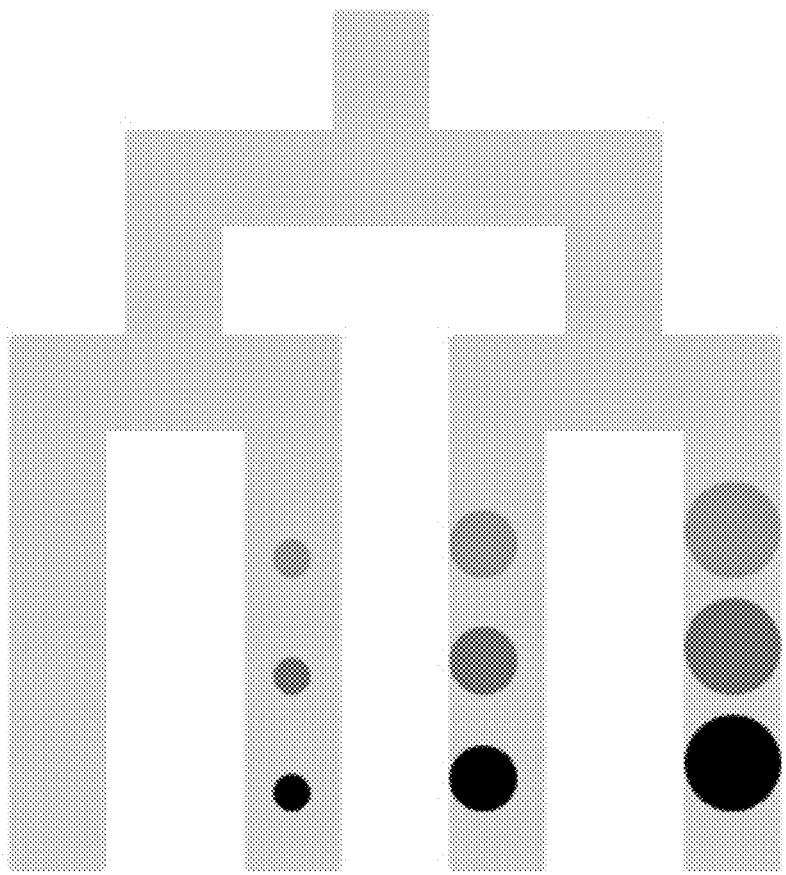
FIG. 6 shows a schematic representation of aliquoting and spiking of subsamples for multi-analyte measurements according to some embodiments herein described. In the representation of FIG. 6, shade indicates type of analog while size indicates lyophilized amount deposited in the channels.

In the illustration of FIG. 6, a binary tree is used to split the sample into multiple channels of equal fluidic resistance, ensuring equal throughput rates. Four channels are shown for simplicity of representation, but it is clear that many more can be constructed along the same binary-tree principle.

Next, circles of different shade of grey indicate lyophilized analogs to different analytes. Within the circles of the same shade, and thus the same analog, some circles are bigger than others, indicating a larger amount deposited in the channel. In the particular example shown in the figure, the leftmost channel is left without a lyophilized spot, to form the "zero-spike" subsample, while the channels receive increasing amount of lyophilized analog of each type the further the right they are on the figure. This is just one of the possible arrangements.

The described approach simultaneously aliquots the sample into equal subsamples and ensures the correct dosage of analogs. Moreover, the shown approach lends itself to simultaneous multi-analyte measurements. Finally, this second embodiment avoids the use of complicated fluid control that is generally necessary in "microfluidic metering" [ref. 53].

The presented results and examples demonstrate, inter alia, sensitive and reliable target detection in microfluidic devices to be used with complex samples, such as biomedical samples.

In particular the above results demonstrate proof of principle for the use of a microfluidic detection system such as a fluorescence immunoassay with human plasma. Vascular Endothelial Growth Factor (VEGF) has been quantified down to 4 pM endogenous concentration. The demonstrated technique is important for detecting techniques such as immunoassay applications in scientific research and "point-of-care" biomedical diagnostics. In particular, the system is immediately applicable to microfluidic quantification of VEGF in human plasma in cancer studies.

However, the significance of the presented proof of principle goes beyond VEGF quantification. The proof makes the system applicable to a broad range of clinical diagnostic tests that require quantifying proteins in human plasma. Thus all such tests currently done in macro-samples could instead be done by the presented microfluidic technique, saving reagents and using micro-samples.

The reduction in required sample volume allows new types of clinical and fundamental studies, e.g. a broad, multianalyte screening of a large number of small-volume samples from existing bio-banks organized by the respective symptomatic pathologies, e.g. multiple sclerosis, particular types of cancer, etc.

For example, patients' histories can be correlated with the results from the microfluidic testing of their banked samples, to discover new pathological expression signatures of high diagnostic and/or predictive value.

Apart from quantifications in fundamental studies, the methods and systems herein described have relevance to routine biomedical diagnostics as well. As an added benefit, the methods and systems herein described are already fully integrable with microfluidic devices for plasma preparation [refs. 42, 47], due to the shared underlying elastomeric microfluidic technology [ref. 48]. Thus our system is an important addition to the technological palette necessary to assemble the future of POC diagnostics.

The examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any devices, methods and materials similar or equivalent to those described herein can be used in the practice for testing of the products, methods and system of the present disclosure, exemplary appropriate products, materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

[1] H. C. Gilbert, J. W. Szokol, Int. Anesthesiol. Clin. 42 (2) (2004) 73.
[2] E. P. Kartalov, J. In-Vitro Diagn. Technol. (2006).
[3] J. Wang, A. Ibanez, M. P. Chatrathi, A. Escarpa, Anal. Chem. 73 (2001) 5323.
[4] J. A. Fruetel, R. F. Renzi, V. A. VanderNoot, J. Stamps, et al., Electrophoresis 26 (2005) 1144.
[5] P. Angenendt, J. Glockler, Z. Konthur, H. Lehrach, D. J. Cahill, Anal. Chem. 75 (2003) 4368.
[6] J. B. Delehanty, F. S. Ligler, Anal. Chem. 74 (2002) 5681.
[7] K. E. Sapsford, P. T. Charles, C. H. Patterson Jr., F. S. Ligler, Anal. Chem. 74 (2002) 1061.
[8] J. R. Sydor, M. Scalf, S. Sideris, G. D. Mao, et al., Anal. Chem. 75 (2003) 6163.
[9] D. Holmes, J. K. She, P. L. Roach, H. Morgan, Lab Chip 7 (2007) 1048.
[10] A. E. Hen, D. J. Throckmorton, A. A. Davenport, A. K. Singh, Anal. Chem. 77 (2005) 585.
[11] M. Wolf, D. Juncker, B. Michel, P. Hunziker, E. Delamarche, Biosens. Bioelectron. 19 (2004) 1193.
[12] J. Yakovleva, R. Davidsson, A. Lobanova, M. Bengtsson, et al., Anal. Chem. 74 (2004) 2994.
[13] A. Chandrasekaran, A. Acharya, J. L. You, K. Y. Soo, et al., Sensors 7 (2007) 1901.
[14] Z. H. Wang, Y. H. Meng, P. Q. Ying, C. Qi, G. Jin, Electrophoresis 27 (2006) 4078.
[15] K. Misiakos, S. E. Kakabakos, P. S. Petrou, H. H. Ruf, Anal. Chem. 76 (2004) 1366.
[16] E. Delamarche, A. Bernard, H. Schmid, B. Michel, H. Biebuyck, Science 276 (1997) 779.
[17] E. Eteshola, M. Balberg, Biomed. Microdev. 6 (1) (2004) 7.
[18] K. S. Phillips, Q. Cheng, Anal. Chem. 77 (2005) 327.
[19] M. E. Piyasena, T. Buranda, Y. Wu, J. Huang, et al., Anal. Chem. 76 (2004) 6266.
[20] V. Kanda, J. K. Kariuki, D. J. Harrison, M. T. McDermott, Anal. Chem. 76 (2004) 7257.
[21] S. K. Sia, V. Linder, B. A. Parviz, A. Siegel, G. M. Whitesides, Angew. Chem. Int. Ed. 43 (2004) 498.
[22] X. Jiang, J. M. K. Ng, A. D. Stroock, S. K. W. Dertinger, G. M. Whitesides, J. Am. Chem. Soc. 125 (2003) 5294.
[23] M. Herrmann, T. Veres, M. Tabrizian, Lab Chip 6 (2006) 555.
[24] M. Herrmann, E. Roy, T. Veres, M. Tabrizian, Lab Chip 7 (2007) 1546.
[25] R. Kurita, Y. Yokota, Y. Sato, F. Mizutani, O. Niwa, Anal. Chem. 78 (2006) 5525.
[26] Y. J. Liu, S. S. Guo, Z. L. Zhang, W. H. Huang, et al., J. Appl. Phys. 102 (2007) 084911.
[27] G. Sui, J. Wang, C. C. Lee, W. Lu, et al., Anal. Chem. 78 (2006) 5543.
[28] V. Linder, E. Verpoorte, N. F. de Rooij, H. Sigrist, W. Thormann, Electrophoresis 23 (2002) 740.
[29] F. Y. H. Lin, M. Sabri, D. Erickson, J. Alirezaie, et al., Analyst 129 (2004) 823.
[30] N. Nashida, W. Satoh, J. Fukuda, H. Suzuki, Biosens. Bioelectron. 22 (2007) 3167.
[31] L. J. Lucas, J. N. Chesler, J. Y. Yoon, Biosens. Bioelectron. 23 (2007) 675.
[32] B. M. Murphy, X. He, D. Dandy, C. S. Henry, Anal. Chem. 80 (2008) 444.
[33] S. H. Kim, Y. Yang, M. Kim, S. W. Nam, et al., Adv. Funct. Mater. 17 (2007) 3493.
[34] Y. Bai, C. G. Koh, M. Boreman, Y. J. Juang, et al., Langmuir 22 (2006) 9458.
[35] K. E. Nelson, J. O. Foley, P. Yager, Anal. Chem. 79 (2007) 3542.
[36] M. J. Pugia, G. Blankenstein, R. P. Peters, J. A. Profitt, et al., Clin. Chem. 51 (10) (2005) 1923.
[37] A. Bhattacharyya, C. M. Klapperich, Biomed. Microdev. 9 (2) (2006) 245.
[38] K. Liang, W. Mu, M. Huang, Z. Yu, Q. Lai, Biomed. Microdev. 9 (3) (2007) 325.
[39] N. Honda, U. Linberg, P. Andersson, S. Hoffmann, H. Takei, Clin. Chem. 51 (10) (2005) 1955.
[40] S. P. Mulvaney, C. L. Cole, M. D. Kniller, M. Malito, et al., Biosens. Bioelectron. 23 (2007) 191.
[41] H. Dong, C. M. Li, Y. F. Zhang, X. D. Cao, Y. Gan, Lab Chip 7 (2007) 1752.
[42] R. Fan, O. Vermesh, A. Srivastava, B. K. H. Yen, L. Qin, H. Ahmad, G. A. Kwong, C. C. Liu, J. Gould, L. Hood, J. R. Heath, Nat. Biotechnol. 26 (12) (2008) 1373.
[43] E. P. Kartalov, J. F. Zhong, A. Scherer, S. R. Quake, et al., Biotechniques 40 (1) (2006) 85.
[44] E. P. Kartalov, D. H. Lin, D. T. Lee, W. F. Anderson, C. R. Taylor, A. Scherer, Electrophoresis 29 (2008) 5010.
[45] H. G. Hotz, O. J. Hines, R. Masood, B. Hotz, T. Foitzik, H. J. Buhr, P. S. Gill, H. R. Reber, Surgery 137 (2) (2005) 192.

[46] A. M. Levine, A. Tulpule, D. I. Quinn, G. Gorospe, D. L. Smith, L. Hornor, W. D. Boswell, B. M. Espina, S. G. Groshen, R. Masood, P. S. Gill, J. Clin. Oncol. 24 (2006) 1712.

[47] V. VanDelinder, A. Groisman, Anal. Chem. 78 (2006) 3765.

[48] E. P. Kartalov, W. F. Anderson, A. Scherer, J. Nanosci. Nanotechnol. 6 (8) (2006) 2265.

[49] Belfort, G., Davis, R. H., and Zydney, A. L. J. Membr. Sci. 96, 1-58 (1994).

[50] Henderson, L. W. Hemofiltration, Springer-Verlag, Berlin, N.Y., (1986).

[51] Zydney, A. L., Colton, C. K. Trans. Am. Soc. Artif. Intern. Organs 28, 408-412 (1982).

[52] Lin, D. H., Taylor, C. R., Anderson, W. F., Scherer, A., Kartalov, E. P. (2009) "Internally calibrated quantification of VEGF in human plasma by fluorescence immunoassays in disposable elastomeric microfluidic devices" *J Chromatography B*.

[53] Hansen, C. L., Sommer, M. O. A., Quake, S. R. (2004) "Systematic investigation of protein behavior with a microfluidic formulator" 101:40, 14431-14436.

[54] A. M. Armani, R. P. Kulkarni, S. E. Fraser, R. C. Flagan, K. J. Vahala, Label-free single-molecule detection with optical microcavities, Science, 317 (2007).

What is claimed is:

1. A method to detect an endogenous target in a sample, the method comprising:

dividing the sample in a plurality of subsamples, each containing the endogenous target, adding to the subsamples set quantities of non-endogenous target and/or analog thereof, the subsamples comprising a subsample with no non-endogenous target nor analog thereof added thereto;

detecting the added non-endogenous target or analog thereof in each subsample thus providing a set of detection signals comprising a detection signal related to the subsample with no non-endogenous target nor analog thereof added thereto;

subtracting a background signal from each detection signal to provide a set of net signals comprising a net signal related to the subsample with no non-endogenous target nor analog thereof added thereto;

providing a distribution of signal points, each signal point based on a net signal of the set of net signals, the signal points comprising a signal point related to the subsample with no non-endogenous target nor analog thereof added thereto, the distribution having a slope; and determining the endogenous target concentration in the sample by dividing the amplitude of the signal point related to the subsample with no non-endogenous target nor analog thereof added thereto by the slope of the distribution.

2. The method of claim 1, wherein the set quantities of the added non-endogenous target and/or analog thereof are determined on the basis of an expected concentration of the endogenous target to be detected.

3. The method of claim 1, wherein the endogenous target comprises multiple targets and the detection of each target or multiple targets is performed in parallel or in series.

4. The method of claim 3, wherein the detection of each endogenous target is performed with a panel of different labeled molecules specific for said each target, each labeled molecule producing a detection signal.

5. The method of claim 1, wherein, before the dividing, the method comprises processing the sample to separate particles or portions thereof.

6. The method of claim 5, wherein the processing is performed by head-on filtration or cross-flow filtration.

7. The method of claim 1, wherein the sample is a biological sample and the target is a biomarker.

8. The method of claim 1, wherein the set quantities of non-endogenous target and/or analog thereof are positioned in lyophilized form on a fluidic pathway of the subsamples from an input towards an area wherein detection is performed.

9. The method of claim 8, wherein the set quantities of non-endogenous target and/or analog thereof are added to the subsamples by microfluidic metering techniques.

10. The method of claim 1, wherein the detection is performed by immunoassay.

* * * * *